United States Patent [19]
Sablong et al.

[11] Patent Number: 6,008,393
[45] Date of Patent: Dec. 28, 1999

[54] IRIDIUM-DIPHOSPINE COMPLEXES AND PROCESS FOR THE HYDROGENATION OF IMINES

[75] Inventors: Rafaël Sablong, Brighton, United Kingdom; John Anthony Osborn, Strasbourg, France; Felix Spindler, Starrkirch-Wil, Switzerland

[73] Assignee: Novartis AG, Basel, Switzerland

[21] Appl. No.: 09/000,071

[22] PCT Filed: Jul. 17, 1996

[86] PCT No.: PCT/EP96/03146

§ 371 Date: Jan. 22, 1998

§ 102(e) Date: Jan. 22, 1998

[87] PCT Pub. No.: WO97/05150

PCT Pub. Date: Feb. 13, 1997

[30] Foreign Application Priority Data

Jul. 27, 1995 [CH] Switzerland ............... 2208/95

[51] Int. Cl.$^6$ ............. C07F 19/00; C07F 15/00; C07F 17/02
[52] U.S. Cl. ............. 556/18; 556/21; 556/28; 556/136; 564/485; 564/500; 548/402
[58] Field of Search ............. 556/18, 21, 28, 556/136; 564/485, 500; 548/402

[56] References Cited

U.S. PATENT DOCUMENTS

| | | | |
|---|---|---|---|
| 3,574,716 | 4/1971 | Coffey | 260/494 |
| 4,994,615 | 2/1991 | Spindler et al. | 564/302 |
| 5,011,995 | 4/1991 | Pugin et al. | 564/302 |
| 5,112,999 | 5/1992 | Osborn et al. | 556/23 |
| 5,371,256 | 12/1994 | Togni et al. | 556/14 |
| 5,563,308 | 10/1996 | Spindler et al. | 585/277 |

FOREIGN PATENT DOCUMENTS

| | | |
|---|---|---|
| 0 419 409 A2 | 9/1990 | European Pat. Off. . |
| 0 419 409 A3 | 9/1990 | European Pat. Off. . |
| 0 564 406 A1 | 3/1993 | European Pat. Off. . |
| 0 612 758 A1 | 2/1994 | European Pat. Off. . |
| 95/21176 | 8/1995 | WIPO . |

OTHER PUBLICATIONS

Z. Anor. Allg. Chem. 519 (1984) 148–154.

*Primary Examiner*—Porfirio Nazario-Gonzalez
*Attorney, Agent, or Firm*—Stephen G. Kalinchak; George R. Dohmann; Gabriel Lopez

[57] ABSTRACT

Compounds of formulae I: $(DIP)IrX_qY_r(Z)$, Ia: $(DIP)IrX_sY_t(Z)_2$ and Ib: $(DIP)Ir(Z)_3$ or mixtures of at least two of those compounds, wherein DIP is a ditertiary diphosphine, the two phosphine groups of which are bonded to a $C_2$-, $C_3$- or $C_4$-carbon chain, with the result that the diphosphine forms a 5- to 7-membered ring together with the Ir atom, X is Cl, Br or I, Y is a hydrogen atom, q and r are 0, 1 or 2 and the sum of q+r is 2, s and t are 0 or 1 and the sum of s+t is 1, and Z is the anion of an organic oxy acid that contains a group C(=O), S(=O)O or P(=O)O in the anion. The compounds are excellent catalysts for the hydrogenation of imines, especially for the enantioselective hydrogenation of prochiral imines.

48 Claims, No Drawings

IRIDIUM-DIPHOSPINE COMPLEXES AND PROCESS FOR THE HYDROGENATION OF IMINES

The present invention relates to iridium-diphosphine complexes having ligands of oxy acids and to a process for the hydrogenation of imines in the presence of such complexes, the hydrogenation being enantioselective when the complex contains chiral diphosphines.

U.S. Pat. No. 4,994,615 describes a process for the asymmetric hydrogenation of prochiral N-arylketimines wherein iridium catalysts having chiral diphosphine ligands are used. U.S. Pat. No. 5,011,995 describes a process for the asymmetric hydrogenation of prochiral N-alkylketimines using the same catalysts. U.S. Pat. No. 5,112,999 discloses polynuclear iridium compounds and a complex salt of iridium, which contain diphosphine ligands, as catalysts for the hydrogenation of imines. U.S. Pat. No. 5,371,256 and EP-A-0 612 758 describe iridium complexes having chiral ferrocenyl diphosphine ligands for the homogeneous enantio-selective hydrogenation of imines.

Those homogeneous catalysis processes have proved valuable, although it is evident, especially in the case of relatively large batches and on an industrial scale, that, depending on the catalyst precursor, the substrate and the diphosphine ligands that are used, the catalysts frequently tend to become deactivated to a greater or lesser extent. In many cases, especially at elevated temperatures—for example at temperatures >25° C., which are necessary for a short reaction time—it is therefore not possible to achieve complete conversion. For industrial applications of the hydrogenation processes, therefore, the catalyst productivity is too low from the point of view of economic viability. Nor is it possible to eliminate those disadvantages by the addition of metal halides as described in U.S. Pat. No. 4,994,615, U.S. Pat. No. 5,011,995 and U.S. Pat. No. 5,112,999.

It has now been found that iridium-diphosphine complexes having at least one ligand of an oxy acid are excellent homogeneous catalysts especially for the enantioselective hydrogenation of imines. It has also been found that the catalyst activity can be increased considerably if the reaction mixture contains a soluble halide and an acid. It has also unexpectedly been found that, with the addition of an acid, the deactivation of the catalysts can be considerably reduced or completely eliminated at the same time. It has also been found, surprisingly, that, with the addition of an acid, at the same time the enantioselectivity when asymmetric catalysts are used is high, and high optical yields even of more than 80% can be achieved, even at reaction temperatures of more than 50° C. It has also unexpectedly been found that, with the addition of an acid, it is even possible at the same time to achieve higher conversions and optical yields with less catalyst, which offers very considerable economic advantages since the molar ratio of imine to iridium catalyst can be greatly increased.

The invention relates to compounds of formulae I, Ia and Ib, or mixtures of at least two of those compounds $(DIP)IrX_qY_r(Z)$ (I), 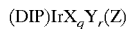

$(DIP)IrX_sY_t(Z)_2$ (Ia), 

$(DIP)Ir(Z)_3$ (Ib), 

wherein

DIP is a ditertiary diphosphine, the two phosphine groups of which are bonded to a $C_2$-, $C_3$- or $C_4$-carbon chain, with the result that the diphosphine forms a 5- to 7-membered ring together with the Ir atom, X is Cl, Br or I, Y is a hydrogen atom, q and r are 0, 1 or 2 and the sum of q+r is 2, s and t are 0 or 1 and the sum of s+t is 1, and Z is the anion of an organic oxy acid that contains a group $C(=O)O$, $S(=O)O$ or $P(=O)O$ in the anion.

The iridium compounds are preferably homogeneous catalysts that are substantially soluble in the reaction medium. The term "catalyst" also includes catalyst precursors that are converted into an active catalyst species at the beginning of a hydrogenation reaction. In the compounds of formulae I, Ia and Ib, DIP is preferably a ditertiary diphosphine (a) the phosphine groups of which are bonded to different carbon atoms of a carbon chain having from 2 to 4 carbon atoms, or (b) the phosphine groups of which are either bonded directly or via a bridge group $—CR_vR_w—$ in the ortho positions of one cyclopentadienyl ring or are bonded to each cyclopentadienyl ring of a ferrocenyl, or (c) one phosphine group of which is bonded to a carbon chain having 2 or 3 carbon atoms and the other phosphine group of which is bonded to an oxygen atom or a nitrogen atom bonded terminally to that carbon chain, or (d) the phosphine groups of which are bonded to the two oxygen atoms or nitrogen atoms bonded terminally to a $C_2$-carbon chain; with the result that in the cases of (a), (b), (c) and (d) a 5-, 6- or 7-membered ring is formed together with the Ir atom, and $R_v$ and $R_w$ are each independently of the other hydrogen, $C_1$–$C_8$alkyl, $C_1$–$C_4$fluoroalkyl, phenyl or benzyl or are phenyl or benzyl each having from 1 to 3 $C_1$–$C_4$alkyl or $C_1$–$C_4$alkoxy substituents. $R_w$ is preferably hydrogen. $R_v$ is preferably $C_1$–$C_4$alkyl and especially methyl.

The diphosphine DIP contains preferably at least one chiral group and is especially an optically pure stereoisomer, or a pair of diastereoisomers, since the use of catalysts containing chiral ligands leads to optical inductions in asymmetric hydrogenation reactions.

The phosphine groups contain preferably two identical or different, preferably identical, unsubstituted or substituted hydrocarbon radicals having from 1 to 20, especially from 1 to 12, carbon atoms. Preference is given to diphosphines wherein the secondary phosphine groups contain two identical or different radicals from the following group: linear or branched $C_1$–$C_{12}$alkyl; unsubstituted or $C_1$–$C_6$alkyl- or $C_1$–$C_6$alkoxy-substituted $C_5$–$C_{12}$-cycloalkyl, $C_5$–$C_{12}$cycloalkyl-$CH_2$—, phenyl or benzyl; and phenyl or benzyl each of which is substituted by halogen (e.g. F, Cl or Br), $C_1$–$C_6$haloalkyl, $(C_1$–$C_{12}$alkyl)$_3$Si, $(C_6H_5)_3$Si, $C_1$–$C_6$haloalkoxy (e.g. trifluoromethoxy), $—NH_2$, phenyl$_2$N—, benzyl$_2$N—, morpholinyl, piperidinyl, pyrrolidinyl, $(C_1$–$C_{12}$alkyl)$_2$N—, -ammonium-$X_1^\ominus$, $—SO_3M_1$, $—CO_2M_1$, $—PO_3M_1$ or by $—COO—C_1$–$C_6$alkyl (e.g. $—COOCH_3$), wherein $M_1$ is an alkali metal or hydrogen and $X_1^\ominus$ is the anion of a monobasic acid. $M_1$ is preferably H, Li, Na or K. $A_1^\ominus$, as the anion of a monobasic acid, is preferably $Cl^\ominus$, $Br^\ominus$ or the anion of a carboxylic acid, for example formate, acetate, trichloroacetate or trifluoroacetate.

Examples of alkyl that preferably contains from 1 to 6 carbon atoms are methyl, ethyl, n-propyl, isopropyl, n-, iso- and tert-butyl and the isomers of pentyl and hexyl. Examples of unsubstituted or alkyl-substituted cycloalkyl are cyclopentyl, cyclohexyl, methyl- or ethyl-cyclohexyl and dimethylcyclohexyl. Examples of alkyl-, alkoxy- or haloalkoxy-substituted phenyl and benzyl are methylphenyl, dimethylphenyl, trimethylphenyl, ethylphenyl, methylbenzyl, methoxyphenyl, dimethoxyphenyl, trifluoromethylphenyl, bis-trifluoromethylphenyl, tristrifluoromethylphenyl, trifluoromethoxyphenyl and bis-trifluoromethoxyphenyl. Preferred phosphine groups are those that contain identical or different, preferably identical, radicals from the group $C_1$–$C_6$alkyl; cyclopentyl and cyclohexyl that are unsubstituted or have from 1 to 3 $C_1$–$C_4$alkyl or $C_1$–$C_4$alkoxy substituents, or benzyl and, especially, phenyl, each of which is unsubstituted or has from 1 to 3 $C_1$–$C_4$alkyl, $C_1$–$C_4$alkoxy, F, Cl, $C_1$–$C_4$fluoroalkyl or $C_1$–$C_4$fluoroalkoxy substituents.

A secondary phosphine group may also be a radical of the formula

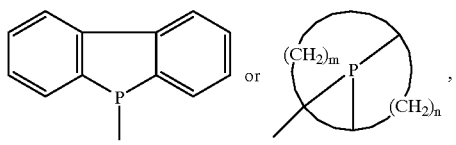

wherein m and n are each independently of the other an integer from 2 to 10, and the sum of m+n is from 4 to 12, especially from 5 to 8. Examples thereof are [3.3.1]- and [4.2.1]-phobyl of the formulae

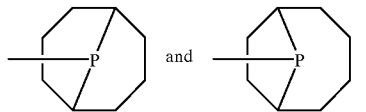

A secondary phosphine group may also be a radical of the formula

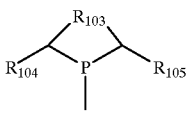

wherein $R_{103}$ is $C_1$–$C_4$alkylene, preferably $C_2$- or $C_3$-alkylene, and $R_{104}$ and $R_{105}$ are each independently of the other hydrogen, $C_1$–$C_6$alkyl, $C_1$–$C_6$alkoxy, $C_1$–$C_6$haloalkyl, $C_5$- or $C_6$-cycloalkyl, phenyl that is unsubstituted or substituted by $C_1$–$C_4$-alkyl, $C_1$–$C_4$alkoxy, $C_1$–$C_4$haloalkyl or by halogen, or benzyl that is unsubstituted or substituted by $C_1$–$C_4$alkyl, $C_1$–$C_4$alkoxy, $C_1$–$C_4$haloalkyl or by halogen.

$R_{104}$ and $R_{105}$ may be, for example, methyl, ethyl, n- or iso-propyl, n-, iso- or tert-butyl, cyclohexyl, phenyl or benzyl. Halogen is preferably F or Cl. Those phosphine groups have further chiral carbon atoms and may be employed in the form of racemates or of diastereoisomers. Of those phosphine ligands, special preference is given to those of the formula

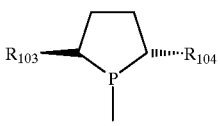

wherein $R_{103}$ and $R_{104}$ are $C_1$–$C_4$alkyl or phenyl.

DIP as a diphosphine is preferably a diphosphine of formula IV, IVa, IVb, IVc or IVd

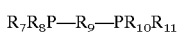

(IV),

(IVa),

(IVb),

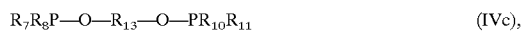

(IVc),

(IVd), wherein $R_7$, $R_8$, $R_{10}$ and $R_{11}$ are each independently of the others a hydrocarbon radical having from 1 to 20 carbon atoms that is unsubstituted or substituted by $C_1$–$C_6$alkyl, $C_1$–$C_6$alkoxy, halogen, $C_1$–$C_6$haloalkyl, $(C_1$–$C_{12}$alkyl$)_3$Si, $(C_6H_5)_3$Si, $C_1$–$C_6$haloalkoxy, —$NH_2$, phenyl$_2$N—, benzyl$_2$N—, morpholinyl, piperidinyl, pyrrolidinyl, $(C_1$–$C_2$alkyl$)_2$N—, -ammonium-$X_1^\ominus$, —$SO_3M_1$, —$CO_2M_1$, —$PO_3M_1$ or by —COO—$C_1$–$C_6$alkyl, wherein $M_1$ is an alkali metal or hydrogen and $X_1^\ominus$ is the anion of a monobasic acid;

$R_7$ and $R_8$ together and $R_{10}$ and $R_{11}$ together are a $C_1$–$C_4$alkylene radical that is unsubstituted or substituted by $C_1$–$C_6$alkyl, $C_1$–$C_6$alkoxy, $C_1$–$C_6$haloalkyl, $C_5$- or $C_6$-cycloalkyl, unsubstituted or $C_1$–$C_4$alkyl-, $C_1$–$C_4$alkoxy-, $C_1$–$C_4$haloalkyl- or halo-substituted phenyl, or by unsubstituted or $C_1$–$C_4$alkyl-, $C_1$–$C_4$alkoxy-, $C_1$–$C_4$haloalkyl- or halo-substituted benzyl;

$R_9$ is linear $C_2$–$C_4$alkylene that is unsubstituted or substituted by $C_1$–$C_6$alkyl, $C_5$- or $C_6$-cycloalkyl, phenyl, naphthyl or by benzyl; 1,2- or 1,3-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl; or 1,2- or 1,3-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl, and in the 1- and/or 2-positions or in the 3-position of which methylene or $C_2$–$C_4$alkylidene is bonded; 1,4butylene substituted in the 2,3-positions by

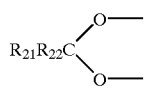

and unsubstituted or substituted in the 1,4-positions by $C_1$–$C_6$alkyl, phenyl or by benzyl, wherein $R_{21}$ and $R_{22}$ are each independently of the other hydrogen, $C_1$–$C_6$alkyl, phenyl or benzyl; 3,4- or 2,4-pyrrolidinylene or 2-methylene-pyrrolidin-4-yl the nitrogen atom of which is substituted by hydrogen, $C_1$–$C_{12}$alkyl, phenyl, benzyl, $C_1$–$C_{12}$alkoxycarbonyl, $C_1$–$C_8$acyl or by $C_1$–$C_{12}$alkylaminocarbonyl; or 1,2-phenylene, 2-benzylene, 1,2-xylylene, 1,8-naphthylene, 2,2'-dinaphthylene or 2,2'-diphenylene, each of which is unsubstituted or substituted by $C_1$–$C_4$alkyl; or $R_9$ is a radical of the formula

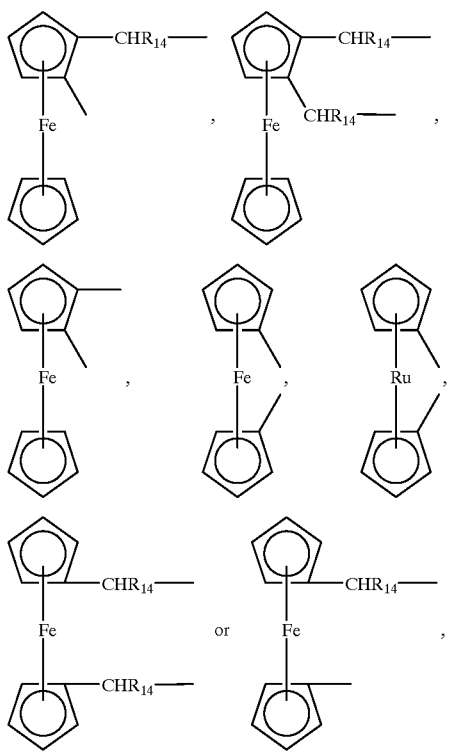

wherein $R_{14}$ is hydrogen, $C_1$–$C_8$alkyl, $C_1$–$C_4$fluoroalkyl, phenyl or phenyl having from 1 to 3 $C_1$–$C_4$alkyl or $C_1$–$C_4$alkoxy substituents;

$R_{12}$ is linear $C_2$- or $C_3$-alkylene that is unsubstituted or substituted by $C_1$–$C_6$alkyl, $C_5$- or $C_6$-cycloalkyl, phenyl, naphthyl or by benzyl; 1,2- or 1,3-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl; or 1,2- or 1,3-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl, and in the 1- and/or 2-positions or in the 3-position of which methylene or $C_2$–$C_4$alkylidene is bonded; 3,4- or 2,4-pyrrolidinylene or 3-methylene-pyrrolidin-4-yl the nitrogen atom of which is substituted by hydrogen, $C_1$–$C_{12}$alkyl, phenyl, benzyl, $C_1$–$C_{12}$alkoxycarbonyl, $C_1$–$C_8$acyl or by $C_1$–$C_{12}$alkylaminocarbonyl; or 1,2-phenylene, 2-benzylene or 1,2-, 2,3- or 1,8-naphthylene, each of which is unsubstituted or substituted by $C_1$–$C_4$alkyl; and $R_{13}$ is linear $C_2$alkylene that is unsubstituted or substituted by $C_1$–$C_6$alkyl, $C_5$- or $C_6$-cycloalkyl, phenyl, naphthyl or by benzyl; 1,2-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl; 3,4pyrrolidinylene the nitrogen atom of which is substituted by hydrogen, $C_1$–$C_{12}$alkyl, phenyl, benzyl, $C_1$–$C_{12}$-alkoxycarbonyl, $C_1$–$C_8$acyl or by $C_1$–$C_{12}$alkylaminocarbonyl; or 1,2-phenylene that is unsubstituted or substituted by $C_1$–$C_4$alkyl, or is a radical, less two hydroxy groups in the ortho positions, of a mono- or di-saccharide; and $R_c$ is hydrogen, $C_1$–$C_4$alkyl, phenyl or benzyl.

$R_7$, $R_8$, $R_{10}$ and $R_{11}$ are preferably identical or different, preferably identical, radicals from the following group: $C_1$–$C_6$alkyl; cyclopentyl and cyclohexyl that are unsubstituted or have from 1 to 3 $C_1$–$C_4$alkyl or $C_1$–$C_4$alkoxy substituents, or benzyl and, especially, phenyl, each of which is unsubstituted or has from 1 to 3 $C_1$–$C_4$alkyl, $C_1$–$C_4$alkoxy, F, Cl, $C_1$–$C_4$fluoroalkyl or $C_1$–$C_4$fluoroalkoxy substituents.

When $R_7$ and $R_8$ together and $R_{10}$ and $R_{11}$ together are each alkylene, they are preferably $C_3$alkylene and especially unsubstituted or substituted $C_2$alkylene. The substituents are especially bonded in the ortho positions relative to the P atom.

A preferred subgroup of diphosphines DIP is formed by those of the formulae

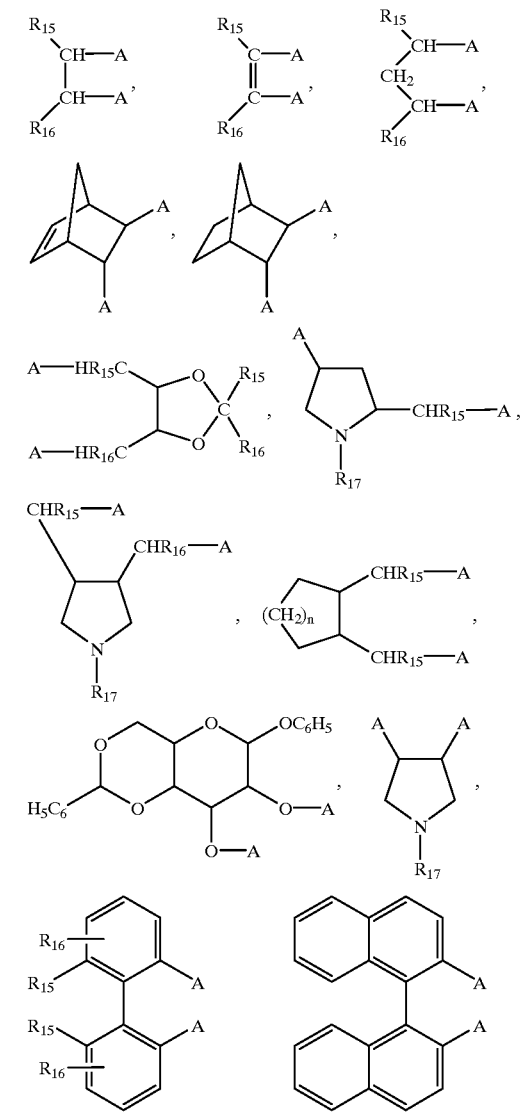

and

-continued

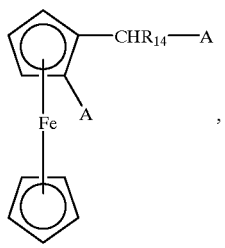

wherin

R$_{15}$ and R$_{16}$ are each independently of the other hydrogen, C$_1$–C$_4$alkyl, phenyl, benzyl, or penyl or benzyl each having from 1 to 3 C$_1$–C$_4$alkyl or C$_1$–C$_4$alhoxy subsituents, R$_{14}$ is hydrogen, C$_1$–C$_4$alkyl, phenyl, benzyl, or phenyl or benzy each having from 1 to 3 C$_1$–C$_4$alkyl or C$_1$–C$_4$alkoxy subsituents, R$_{17}$ is hydrogen, C$_1$–C$_4$alkyl, phenyl, benzyl, C$_1$–C$_6$alkoxy-CO—, C$_1$–C$_6$alkyl-CO—, phenyl-CO—, naphthyl-CO— or C$_1$–C$_4$alkylNH-CO—, A may be identical or different groups —P(R)$_2$, wherein R is C$_1$–C$_6$alkylyl, cyclohexyl, phenyl, benzyl, or phenyl or benzyl each having from 1 to 3 C$_1$–C$_4$alkyl, dosubstituted amino, C$_1$–C$_4$alkoxy, —CF$_3$ or parially or fully fluorinated C$_1$–C$_4$alkoxy substituents, and n is 0, 1 or 2.

Of those phosphines, chirally substituted compounds are especially preferred.

Some preferred examples of diphosphines DIP are as follows (PH is phenyl):

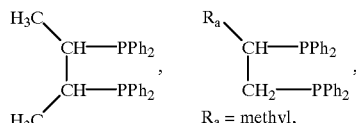

R$_a$ = methyl, cyclohexyl, phenyl

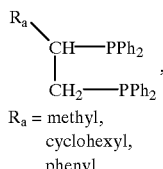

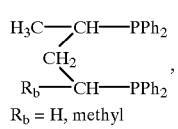

R$_b$ = H, methyl

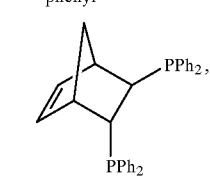

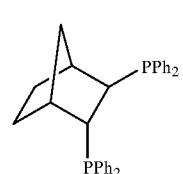

R$_c$ = H, methyl, phenyl
R$_d$ = H, methyl, phenyl

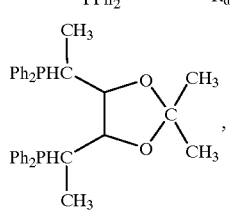

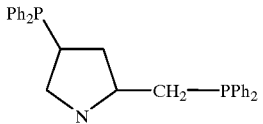

R$_e$ = —CO$_2$-tert-butyl,
—CO-tert-butyl,
H, —CO-phenyl,
—CO—NH—C$_1$–C$_4$alkyl R$_f$ = C$_1$–C$_4$alkyl, benzyl

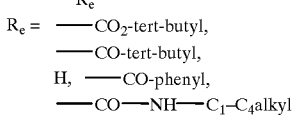

n = 0, 1 or 2

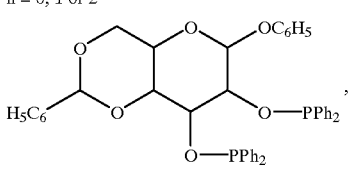

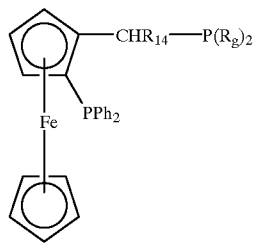

R$_{14}$ = C$_1$–C$_4$alkyl, especially methyl,
R$_g$ = phenyl or cyclohexyl that is unsubstituted or has from 1 to 3 methyl, disubstituted amino, —CF$_3$ or methoxy substituents Especially suitable diphosphine ligands DIP are those wherein the secondary phosphine groups are either bonded directly or via a bridge group —CR$_a$R$_b$— in the ortho positions of one cyclopentadienyl ring or are bonded to each cyclopentadienyl ring of a ferrocenyl, most especially those of formula X

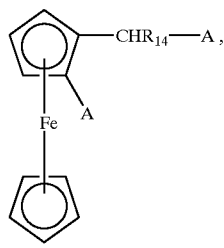

(X)

wherein

R$_{14}$ is hydrogen, C$_1$–C$_4$alkyl, phenyl, benzyl, or phenyl or benzyl each having from 1 to 3 C$_1$–C$_4$alkyl or C$_1$–C$_4$alkoxy substituents, and A may be identical or different groups —P(R)$_2$, wherein R is C$_1$–C$_6$alkyl, cyclohexyl, phenyl, benzyl, or phenyl or benzyl each having from 1 to 3 C$_1$–C$_4$alkyl, disubstituted amino, $C_1$–$C_4$alkoxy, —$CF_3$ or partially or fully fluorinated $C_1$–$C_4$alkoxy substituents.

In a preferred subgroup, the diphosphine of formula X is chiral and $R_{14}$ is $C_1$–$C_4$alkyl, or phenyl or benzyl each having from 1 to 3 $C_1$–$C_4$alkyl or $C_1$–$C_4$alkoxy substituents, and A may be identical or different groups —$P(R)_2$, wherein R is $C_1$–$C_6$alkyl, cyclohexyl, phenyl, benzyl, or phenyl or benzyl each having from 1 to 3 $C_1$–$C_4$alkyl, disubstituted amino, $C_1$–$C_4$alkoxy, —$CF_3$ or partially or fully fluorinated $C_1$–$C_4$alkoxy substituents.

Of the above, very special preference is given to the following diphosphine ligands:

{(R)-1-[(S)-2-(diphenylphosphino)ferrocenyl]}ethyl-di(3,5-dimethylphenyl)phosphine {(R)-1-[(S)-2-(diphenylphosphino)ferrocenyl]}ethyl-di(3,5-dimethyl-4-N,N-dipropylaminophenyl)phosphine {(R)-1-[(S )-2-(diphenylphosphino)ferrocenyl]}ethyl-di(3,5-di-isopropyl-4-N,N-dimethylaminophenyl)phosphine {(R)-1-[(S)-2-(diphenylphosphino)ferrocenyl]}ethyl-di(3,5-di-isopropyl-4-N,N-dibenzylylaminophenyl)phosphine {(R)-1-[(S)-2-(diphenylphosphino)ferrocenyl]}ethyl-di(3,5-dimethyl-4-N,N-dibenzylylaminophenyl)phosphine {(R)-1-[(S)-2-(diphenylphosphino)ferrocenyl]}ethyl-di(3,5-dimethyl-4-(1'-pyrrolo)-phenyl)phosphine {(R)-1-[(S)-2-(diphenylphosphino)ferrocenyl]}ethyl-di(3,5-dimethyl-4-N,N-dipentylaminophenyl)phosphine {(R)-1-[(S)-2-(diphenylphosphino)ferrocenyl]}ethyl-di(3,5-dimethyl-4-N,N-dimethylaminophenyl)phosphine 1,4-bis(diphenylphosphino)butane {(R)-1-[(S)-2-di(4-methoxyphenyl)phosphino)ferrocenyl]}ethyl-di(3,5-dimethyl-4-N,N-dimethylaminophenyl)phosphine and most especially {(R)-1-[(S)-2-(diphenylphosphino)ferrocenyl]}ethyl-di(3,5-dimethylphenyl)phosphine.

Suitable diphosphines and diphosphinites have been described, for example, by H. B. Kagan in Chiral Ligands for Asymmetric Catalysis, Asymmetric Synthesis, Volume 5, pp. 13–23, Academic Press, Inc., N.Y. (1985). The preparation of ferrocenyl diphosphine ligands is described, for example, in EP-A-0 564 406, by T. Hayashi et al. in Bull. Chem. Soc. Jpn., 53, pages 1136–1151, and by A. Togni et al. in J. Am. Chem. Soc., 116, pages 4062 to 4066 (1994) and Inorg. Chim. Acta, 222, pages 213–224.

In formulae I and Ia, X is preferably Br or I and especially I. In formula I, q and r are each preferably 1. In formula Ia, s is preferably 0 and t is preferably 1. In a preferred subgroup, the compounds according to the invention are of formulae Ib, Ic and Id (DIP)Ir(Z)$_3$ (Ib), (DIP)IrIH(Z) (Ic), (DIP)IrH(Z)$_2$ (Id), wherein Z is the anion of an organic oxy acid that contains a group C(=O)O, S(=O)O or P(=O)O in the anion.

The organic oxy acid may be mono- or poly-basic, for example mono- or di-basic. Monobasic acids are especially preferred; in the case of polybasic acids, the excess acidic OH groups may be blocked, for example by esterification.

The organic oxy acid may be, for example, a partial ester of an at least dibasic inorganic oxy acid, preferably those of formula A or B $R_{100}$—$OSO_2$—OH (A), $(R_{100}$—$O)_2$P(O)—OH (B), wherein $R_{100}$ is the monovalent radical of an aliphatic, cycloaliphatic, cycloaliphatic-aliphatic, aromatic or araliphatic alcohol having from 1 to 20 carbon atoms, preferably from 1 to 12 carbon atoms and especially from 1 to 8 carbon atoms.

$R_{100}$ may be, for example, branched and, preferably, linear $C_1$–$C_{20}$alkyl, preferably $C_1$–$C_{12}$alkyl and especially $C_1$–$C_8$alkyl. Some examples are methyl, ethyl, propyl, butyl, pentyl, hexyl, octyl, decyl and dodecyl.

$R_{100}$ may be, for example, $C_3$–$C_8$cycloalkyl and preferably $C_5$- or $C_6$-cycloalkyl. Some examples are cyclopropyl, cyclobutyl, cyclopentyl, cyclohexyl, cycloheptyl and cyclooctyl.

$R_{100}$ may be, for example, $C_3$–$C_8$cycloalkyl-$(CH_2)_p$— and preferably $C_5$- or $C_6$-cycloalkyl-$(CH_2)_p$—, wherein p is a number from 1 to 4 and is preferably 1 or 2. Some examples are cyclopropyl-$CH_2$—, cyclobutyl-$CH_2$—, cyclopentyl-$CH_2$—, cyclohexyl-$CH_2$—, cycloheptyl-$CH_2$—, cyclooctyl-$CH_2$—, cyclopropyl-$CH_2$—$CH_2$—, cyclobutyl-$CH_2$—$CH_2$—, cyclopentyl-$CH_2$—$CH_2$—, cyclohexyl-$CH_2$—$CH_2$—, cycloheptyl-$CH_2$—$CH_2$—, cyclooctyl-$CH_2$—$CH_2$—.

$R_{100}$ may be, for example, $C_6$–$C_{16}$aryl, preferably $C_6$–$C_{10}$aryl and especially phenyl.

$R_{100}$ may be, for example, $C_6$–$C_{16}$aryl-$(CH_2)_p$—, preferably $C_6$–$C_{10}$aryl-$(CH_2)_p$— and especially phenyl-$(CH_2)_p$—, wherein p is a number from 1 to 4 and is preferably 1 or 2. Some examples are benzyl, phenylethyl and naphthylmethyl.

The organic oxy acid is preferably of formula C, D or E $R_{101}$—S(O)$_k$—OH (C), $R_{101}(R_{100}O)_l$P(O)—OH (D), $R_{102}$—C(O)—OH (E), wherein k is 1 or 2, l is 0 or 1, $R_{100}$ is the monovalent radical of an aliphatic, cycloaliphatic, cycloaliphatic-aliphatic, aromatic or araliphatic alcohol having from 1 to 20 carbon atoms, preferably from 1 to 12 carbon atoms and especially from 1 to 8 carbon atoms, $R_{101}$ is an aliphatic, cycloaliphatic, cycloaliphatic-aliphatic, aromatic or araliphatic radical having from 1 to 20 carbon atoms, preferably from 1 to 12 carbon atoms and especially from 1 to 8 carbon atoms, that is unsubstituted or mono- or poly-substituted by $C_1$–$C_6$-alkyl, $C_1$–$C_6$hydroxyalkyl, $C_1$–$C_6$haloalkyl (especially fluoro- or chloro-alkyl), $C_1$–$C_6$-alkoxy, $C_1$–$C_6$alkylthio, $C_5$- or $C_6$-cycloalkyl, $C_6$–$C_{10}$aryl, —OH, —F, Cl, Br, —CN, —$NO_2$ or by —C(O)O—$C_1$–$C_6$alkyl, it being possible for the substituents cycloalkyl and aryl to be substituted by $C_1$–$C_6$alkyl, $C_1$–$C_6$alkoxy, —OH, —F, —Cl, —Br, —CN, —$NO_2$, $C_1$–$C_6$haloalkyl or by —C(O)O—$C_1$–$C_6$alkyl, and $R_{102}$ is hydrogen or has independently the same meaning as given for $R_{101}$.

For $R_{100}$, the examples and preferences mentioned hereinbefore apply.

In formula C, k is preferably 2.

$R_{101}$ and $R_{102}$ may be, for example, branched and, preferably, linear $C_1$–$C_{20}$alkyl, preferably $C_1$–$C_{12}$alkyl and especially $C_1$–$C_8$alkyl. Some examples are methyl, ethyl, propyl, butyl, pentyl, hexyl, octyl, decyl and dodecyl.

$R_{101}$ and $R_{102}$ may be, for example, $C_3$–$C_8$cycloalkyl and preferably $C_5$- or $C_6$-cycloalkyl. Some examples are cyclopropyl, cyclobutyl, cyclopentyl, cyclohexyl, cycloheptyl and cyclooctyl.

$R_{101}$ and $R_{102}$ may be, for example, $C_3$–$C_8$cycloalkyl-$(CH_2)_p$— and preferably $C_5$- or $C_6$-cycloalkyl-$(CH_2)_p$—, wherein p is a number from 1 to 4 and is preferably 1 or 2. Some examples are cyclopropyl-$CH_2$—, cyclobutyl-$CH_2$—, cyclopentyl-$CH_2$—, cyclohexyl-$CH_2$—, cycloheptyl-$CH_2$—, cyclooctyl-$CH_2$—, cyclopropyl-$CH_2$—$CH_2$—, cyclobutyl-$CH_2$—$CH_2$—, cyclopentyl-$CH_2$—$CH_2$—, cyclohexyl-$CH_2$—$CH_2$—, cycloheptyl-$CH_2$—$CH_2$— and cyclooctyl-$CH_2$-$CH_2$—.

$R_{101}$ and $R_{102}$ may be, for example, $C_6$–$C_{16}$aryl, preferably $C_6$–$C_{10}$aryl and especially phenyl.

$R_{101}$ and $R_{102}$ may be, for example, $C_6$–$C_{16}$aryl-$(CH_2)_p$—, preferably $C_6$–$C_{10}$aryl-$(CH_2)_p$— and especially phenyl-$(CH_2)_p$—, wherein p is a number from 1 to 4 and is preferably 1 or 2. Some examples are benzyl, phenylethyl and naphthylmethyl.

In a preferred form, the organic acids are of formulae C1 and E1

$$R_{101}\text{—S(O)}_2\text{—OH} \qquad (C1),$$

$$R_{101}\text{—C(O)—OH} \qquad (E1),$$

wherein $R_{101}$ is unsubstituted or $C_1$–$C_4$alkyl-, $C_1$–$C_4$alkoxy-, —OH—, —F—, —Cl—, —Br—, —$NO_2$—, —C(O)O—$C_1$–$C_4$alkyl-, cyclopentyl-, cyclohexyl- or phenyl-substituted $C_1$–$C_6$alkyl, preferably $C_1$–$C_4$alkyl, $C_5$- or $C_6$-cycloalkyl or phenyl, it being possible for the substituents cyclopentyl, cyclohexyl or phenyl to be substituted by $C_1$–$C_4$alkyl, $C_1$–$C_4$-alkoxy, —F, —Cl, —Br or by $C_1$–$C_4$haloalkyl.

Some examples of preferred organic acids are acetic acid, propionic acid, butyric acid, mono-, di- or tri-chloro- or mono-, di- or tri-fluoro-acetic acid, perfluoropropionic acid, cyclohexanecarboxylic acid, benzoic acid, mono-, di- or tri-methylbenzoic acid, fluoro- or chloro-benzoic acid, trifluoromethylbenzoic acid, phenylacetic acid, methanesulfonic acid, ethanesulfonic acid, propanesulfonic acid, butanesulfonic acid, mono-, di- or tri-chloro- or mono-, di- or tri-fluoro-methanesulfonic acid, benzenesulfonic acid, mono-, di- or tri-methylbenzenesulfonic acid and fluoro- or chloro-benzenesulfonic acid.

The compounds of formula I are generally crystalline substances that are obtainable starting from the iridium-diphosphine complexes described in EP-A-0 419 409 or iridium-diphosphine complexes that can be prepared analogously. The compounds of formula I may also be mixtures of position isomers.

The invention relates also to a process for the preparation of compounds of formula I, Ia or Ib or mixtures of at least two of those compounds, which comprises reacting an iridium compound of formula F $$[(DIP)IrX_uY_v]_2 \qquad (F),$$

wherein
DIP is as defined hereinbefore,
X is Cl, Br or I,
Y is hydrogen,
u is 2 or 3, v is 0 or 1, and the sum of u+v is 3, with at least equivalent amounts of a metal salt of formula G $$MeZ \qquad (G),$$

wherein Z is the anion of an organic oxy acid that contains a group C(=O)O, S(=O)O or P(=O)O in the anion, and Me is a metal ion that forms with the halide X a metal halide MeX that is not readily soluble.

The metal ion Me may be, for example, $Hg^{2\oplus}$, $Ti^{61}$, $Hg_2^{2\oplus}$, $Cu^{2\oplus}$ and, especially, $Ag^{\oplus}$.

The reaction is advantageously carried out in an inert solvent or a mixture of inert solvents. Examples of suitable solvents are hydrocarbons (petroleum ether, hexane, heptane, cyclohexane, methylcyclohexane, benzene, toluene and xylene), halogenated hydrocarbons (methylene chloride, chloroform, carbon tetrachloride, 1,1,2-trichloroethane, 1,1,2,2,-tetrachloroethane, chlorobenzene), ethers (diethyl ether, dibutyl ether, ethylene glycol dimethyl or diethyl ether, tetrahydrofuran, dioxane), carboxylic acid esters, ketones, N-dialkylated carboxylic acid amides and N-alkylated lactams. Preferred solvents are hydrocarbons and halogenated hydrocarbons.

The reaction can be carried out, for example, at temperatures of from 0 to 200° C., preferably from 20 to 150° C. and especially from 20 to 100° C.

In the preparation of the compounds of formula I, at least 2 mol of compound of formula G are preferably used per mole of compound of formula F, and a slight excess of up to 0.2 equivalents may be advantageous. For the preparation of the compounds of formula Ia, preferably at least 4 mol of compound of formula G are used per mole of compound of formula F, and a slight excess of up to 0.2 equivalents may be advantageous. In the preparation of the compounds of formula Ib, preferably at least 6 mol of compound of formula G are used per mole of compound of formula F, and a slight excess of up to 0.2 equivalents may be advantageous. The compounds of formulae Ia and Ib can also be prepared from 1 mol of the compounds of formula I by reaction with 1 mol or 2 mol, respectively, of compound of formula G. When the compounds of formula I are used as starting material, the concentration ratio of the compound of formula I to the compound of formula G determines whether pure compounds of formulae I, Ia and Ib or mixtures of such compounds are formed.

The compounds according to the invention are usually solid or crystalline and are obtained in high yields. They can be isolated in a simple manner by filtration and can be purified, if desired, by customary methods, for example by fractional crystallisation or chromato-graphic methods. Using the same methods, individual compounds and even position isomers, which are clearly also formed, can be isolated from mixtures of compounds. Isolation is not, however, necessary for subsequent use since the mixtures also have catalytic activity.

The compounds according to the invention are excellently suitable for the catalytic hydrogenation of imines, it being possible to obtain high conversions in short periods of time. The compounds according to the invention that have chiral diphosphine ligands are suitable especially for the hydrogenation of prochiral imines for the preparation of optically pure amines.

The invention relates also to a process for the hydrogenation of imines with hydrogen under elevated pressure in the presence of iridium catalysts containing diphosphine ligands, with or without an inert solvent, wherein the hydrogenation is carried out in the presence of at least one compound of formula I, Ia or Ib, or mixtures of at least two of those compounds, $$(DIP)IrX_qY_r(Z) \qquad (I),$$

$$(DIP)IrX_sY_t(Z)_2 \qquad (Ia),$$

$$(DIP)Ir(Z)_3 \qquad (Ib),$$

wherein

DIP is a ditertiary diphosphine, the two phosphine groups of which are bonded to a $C_2$-, $C_3$- or $C_4$-carbon chain, with the result that the diphosphine forms a 5- to 7-membered ring together with the Ir atom, X is Cl, Br or I, Y is a hydrogen atom, q and rare 0, 1 or 2 and the sum of q+r is 2, s and t are 0 or 1 and the sum of s+t is 1, and Z is the anion of an organic oxy acid that contains a group $C(=O)O$, $S(=O)O$ or $P(=O)O$ in the anion.

Suitable imines are especially those that contain at least one

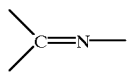

group. If the groups are substituted asymmetrically and are thus compounds having a prochiral ketimine group, it is possible in the process according to the invention for mixtures of optical isomers or pure optical isomers to be formed if enantioselective or diastereo-selective iridium catalysts are used. The imines may contain further chiral carbon atoms. The free bonds in the above formulae may be saturated with hydrogen or organic radicals having from 1 to 22 carbon atoms or organic hetero radicals having from 1 to 20 carbon atoms and at least one hetero atom from the group O, S, N and P. The nitrogen atom of the group

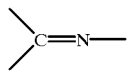

may also be saturated with $NH_2$ or a primary amino group having from 1 to 22 carbon atoms or a secondary amino group having from 2 to 40 carbon atoms. The organic radicals may be substituted, for example, by F, Cl, Br, $C_1$–$C_4$haloalkyl wherein halogen is preferably F or Cl, —CN, —$NO_2$, —$CO_2H$, —$CONH_2$, —$SO_3H$, —$PO_3H_2$, or by $C_1$–$C_{12}$alkyl esters or $C_1$–$C_{12}$alkylamides, phenyl esters or benzyl esters of the groups —$CO_2H$, —$SO_3H$ and —$PO_3H_2$. Aldimine and ketimine groups are especially reactive, with the result that using the process according to the invention it is possible selectively to hydrogenate

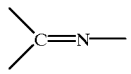

groups in addition to the

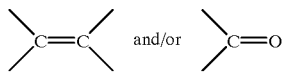

groups. Aldimine and ketimine groups are also to be understood to include

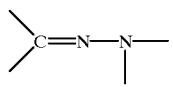

hydrazone groups.

The process according to the invention is suitable especially for the hydrogenation of aldimines, ketimines and hydrazones with the formation of corresponding amines and hydrazines, respectively. The ketimines are preferably N-substituted. It is preferable to use chiral iridium catalysts and to hydrogenate enantiomerically pure, chiral or prochiral ketimines to prepare optical isomers, the optical yields (enantiomeric excess, ee) being, for example, higher than 30%, preferably higher than 50%, and yields of more than 90% being achievable. The optical yield indicates the ratio of the two stereoisomers formed, which ratio is, for example, greater than 2:1 and preferably greater than 4:1.

The imines are preferably imines of formula II

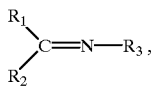

(II)

which are hydrogenated to form amines of formula III

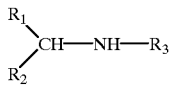

(III)

wherein $R_3$ is preferably a substituent and wherein $R_3$ is linear or branched $C_1$–$C_{12}$alkyl, cycloalkyl having from 3 to 8 ring carbon atoms; heterocycloalkyl bonded via a carbon atom and having from 3 to 8 ring atoms and 1 or 2 hetero atoms from the group O, S and $NR_6$; a $C_7$–$C_{16}$aralkyl bonded via an alkyl carbon atom or $C_1$–$C_{12}$alkyl substituted by the mentioned cycloalkyl or heterocycloalkyl or heteroaryl;

or wherein $R_3$ is $C_6$–$C_{12}$aryl, or $C_4$–$C_{11}$heteroaryl bonded via a ring carbon atom and having 1 or 2 hetero atoms in the ring; $R_3$ being unsubstituted or substituted by —CN, —$NO_2$, F, Cl, $C_1$–$C_{12}$alkyl, $C_1$–$C_{12}$alkoxy, $C_1$–$C_{12}$alkylthio, $C_1$–$C_6$haloalkyl, —OH, $C_6$–$C_{12}$-aryl or -aryloxy or -arylthio, $C_7$–$C_{16}$-aralkyl or -aralkoxy or -aralkylthio, secondary amino having from 2 to 24 carbon atoms, —$CONR_4R_5$ or by —$COOR_4$, and the aryl radicals and the aryl groups in the aralkyl, aralkoxy and aralkylthio in turn being unsubstituted or substituted by —CN, —$NO_2$, F, Cl, $C_1$–$C_4$-alkyl, -alkoxy or -alkylthio, —OH, —$CONR_4R_5$ or by —$COOR_4$;

$R_4$ and $R_5$ are each independently of the other hydrogen, $C_1$–$C_{12}$alkyl, phenyl or benzyl, or $R_4$ and $R_5$ together are tetra- or penta-methylene or 3-oxapentylene;

$R_6$ has independently the same meaning as given for $R_4$;

$R_1$ and $R_2$ are each independently of the other a hydrogen atom, $C_1$–$C_{12}$alkyl or cycloalkyl having from 3 to 8 ring carbon atoms, each of which is unsubstituted or substituted by —OH, $C_1$–$C_{12}$alkoxy, phenoxy, benzyloxy, secondary amino having from 2 to 24 carbon atoms, —$CONR_4R_5$ or by —$COOR_4$; $C_6$–$C_{12}$aryl or $C_7$–$C_{16}$aralkyl that is unsubstituted or substituted as $R_3$, or —$CONR_4R_5$ or —$COOR_4$, wherein $R_4$ and $R_5$ are as defined hereinbefore; or $R_3$ is as defined hereinbefore and $R_1$ and $R_2$ together are alkylene having from 2 to 5 carbon atoms that is optionally interrupted by 1 or 2 —O—, —S— or —$NR_6$— radicals, and/or unsubstituted or substituted by =O or as $R_1$ and $R_2$ above in the meaning of alkyl, and/or condensed with benzene, pyridine, pyrimidine, furan, thiophene or pyrrole; or $R_2$ is as defined hereinbefore and $R_1$ and $R_3$ together are alkylene having from 2 to 5 carbon atoms that is optionally interrupted by 1 or 2 —O—, —S— or —$NR_6$— radicals, and/or unsubstituted or substituted by =O or as $R_1$ and $R_2$ above in the meaning of alkyl, and/or condensed with benzene, pyridine, pyrimidine, furan, thiophene or pyrrole.

The radicals $R_1$, $R_2$ and $R_3$ may contain one or more chirality centres.

$R_1$, $R_2$ and $R_3$ can be substituted in any desired positions by identical or different radicals, for example by from 1 to 5, preferably from 1 to 3, substituents.

Suitable substituents for $R_1$ and $R_2$ and $R_3$ are: $C_1$–$C_{12}$-, preferably $C_1$–$C_6$- and especially $C_1$–$C_4$-alkyl, -alkoxy or -alkylthio, e.g. methyl, ethyl, propyl, n-, iso- and tert-butyl, the isomers of pentyl, hexyl, octyl, nonyl, decyl, undecyl and dodecyl, and corresponding alkoxy and alkylthio radicals; $C_1$–$C_6$-, preferably $C_1$–$C_4$-haloalkyl having preferably F and Cl as halogen, e.g. trifluoro- or trichloro-methyl, difluorochloromethyl, fluorodichloromethyl, 1,1-difluoroeth-1-yl, 1,1-dichloroeth-1-yl, 1,1,1-trichloro- or 1,1,1-trifluoroeth-2-yl, pentachloroethyl, pentafluoroethyl, 1,1,1-trifluoro-2,2-dichloroethyl, n-perfluoropropyl, iso-perfluoropropyl, n-perfluorobutyl, fluoro- or chloro-methyl, difluoro- or dichloro-methyl, 1-fluoro- or 1-chloro-eth-2-yl or -eth-1-yl, 1-, 2- or 3-fluoro- or 1-, 2- or 3-chloro-prop-1-yl or -prop-2-yl or -prop-3-yl, 1-fluoro- or 1-chloro-but-1-yl, -but-2-yl, -but-3-yl or -but-4yl, 2,3-dichloro-prop-1-yl, 1-chloro-2-fluoro-prop3-yl and 2,3-dichlorobut-1-yl; $C_6$–$C_{12}$-aryl, -aryloxy or -arylthio, in which aryl is preferably naphthyl and especially phenyl, $C_7$–$C_{16}$-aralkyl, -aralkoxy and -aralkylthio, in which the aryl radical is preferably naphthyl and especially phenyl and the alkylene radical is linear or branched and contains from 1 to 10, preferably from 1 to 6 and especially from 1 to 3 carbon atoms, for example benzyl, naphthylmethyl, 1- or 2-phenyl-eth-1-yl or -eth-2-yl, 1-, 2- or 3-phenyl-prop-1-yl, -prop-2-yl or -prop-3-yl, with benzyl being especially preferred;

the radicals containing the aryl groups mentioned above may in turn be mono- or poly-substituted, for example by $C_1$–$C_4$-alkyl, -alkoxy or -alkylthio, halogen, —OH, —$CONR_4R_5$ or by —$COOR_5$, wherein $R_4$ and $R_5$ are as defined; examples are methyl, ethyl, n- and iso-propyl, butyl, corresponding alkoxy and alkylthio radicals, F, Cl, Br, dimethyl-, methylethyl- and diethyl-carbamoyl and methoxy-, ethoxy-, phenoxy- and benzyloxy-carbonyl;

halogen, preferably F and Cl;

secondary amino having from 2 to 24, preferably from 2 to 12 and especially from 2 to 6 carbon atoms, the secondary amino preferably containing 2 alkyl groups, for example dimethyl-, methylethyl-, diethyl-, methylpropyl-, methyl-n-butyl-, di-n-propyl-, di-n-butyl-, di-n-hexyl-amino;

—$CONR_4R_5$, wherein $R_4$ and $R_5$ are each independently of the other $C_1$–$C_{12}$-, preferably $C_1$–$C_6$- and especially $C_1$–$C_4$-alkyl, or $R_4$ and $R_5$ together are tetra- or penta-methylene or 3-oxapentylene, the alkyl being linear or branched, e.g. dimethyl-, methylethyl-, diethyl-, methyl-n-propyl-, ethyl-n-propyl-, di-n-propyl-, methyl-n-butyl-, ethyl-n-butyl-, n-propyl-n-butyl- and di-n-butyl-carbamoyl;

—$COOR_4$, wherein $R_4$ is $C_1$–$C_{12}$-, preferably $C_1$–$C_6$-alkyl, which may be linear or branched, e.g. methyl, ethyl, n- and iso-propyl, n-, iso- and tert-butyl, and the isomers of pentyl, hexyl, heptyl, octyl, nonyl, decyl, undecyl and dodecyl.

$R_1$, $R_2$ and $R_3$ may contain especially functional groups, for example keto groups, —CN, —$NO_2$, carbon double bonds, N—O—, aromatic halogen groups and amide groups.

$R_1$ and $R_2$ as heteroaryl are preferably a 5- or 6membered ring having 1 or 2 identical or different hetero atoms, especially O, S or N, which contains preferably 4 or 5 carbon atoms and can be condensed with benzene. Examples of heteroaromatics from which $R_1$ can be derived are furan, pyrrole, thiophene, pyridine, pyrimidine, indole and quinoline.

$R_1$ and $R_2$ as heteroaryl-substituted alkyl are derived preferably from a 5- or 6-membered ring having 1 or 2 identical or different hetero atoms, especially O, S or N, which contains preferably 4 or 5 carbon atoms and can be condensed with benzene. Examples of heteroaromatics are furan, pyrrole, thiophene, pyridine, pyrimidine, indole and quinoline.

$R_1$ and $R_2$ as heterocycloalkyl or as heterocycloalkyl-substituted alkyl contain preferably from 4 to 6 ring atoms and 1 or 2 identical or different hetero atoms from the group O, S and $NR_6$. It can be condensed with benzene. It may be derived, for example, from pyrrol-idine, tetrahydrofuran, tetrahydrothiophene, indane, pyrazolidine, oxazolidine, piperidine, piperazine or morpholine.

$R_1$, $R_2$ and $R_3$ as alkyl are preferably unsubstituted or substituted $C_1$–$C_6$-, especially $C_1$–$C_4$-alkyl, which may be linear or branched. Examples are methyl, ethyl, iso- and n-propyl, iso-, n- and tert-butyl, the isomers of pentyl, hexyl, heptyl, octyl, nonyl, decyl, undecyl and dodecyl.

$R_1$, $R_2$ and $R_3$ as unsubstituted or substituted cycloalkyl contain preferably from 3 to 6, especially 5 or 6, ring carbon atoms. Examples are cyclopropyl, cyclobutyl, cyclopentyl, cyclohexyl, cycloheptyl and cyclooctyl.

$R_1$, $R_2$ and $R_3$ as aryl are preferably unsubstituted or substituted naphthyl and especially phenyl. $R_1$, $R_2$ and $R_3$ as aralkyl are preferably unsubstituted or substituted phenyla-lkyl having from 1 to 10, preferably from 1 to 6 and especially from 1 to 4 carbon atoms in the alkylene, the alkylene being linear or branched. Examples are especially benzyl, and 1-phenyleth-1-yl, 2-phenyleth-1-yl, 1-phenylprop-1-yl, 1-phenylprop-2-yl, 1-phenylprop-3-yl, 2-phenylprop-1-yl, 2-phenylprop-2-yl and 1-phenylbut-4-yl.

In $R_2$ and $R_3$ as —$CONR_4R_5$ and —$COOR_4$, $R_4$ and $R_5$ are preferably $C_1$–$C_6$-, especially $C_1$–$C_4$-alkyl, or $R_4$ and $R_5$ together are tetramethylene, pentamethylene or 3-oxapentylene. Examples of alkyl are mentioned hereinbefore.

$R_1$ and $R_2$ together or $R_1$ and $R_3$ together as alkylene are preferably interrupted by 1 —O—, —S— or —$NR_6$— radical, preferably —O—. $R_1$ and $R_2$ together or $R_1$ and $R_3$ together form, with the carbon atom or with the —N=C group to which they are bonded, respectively, preferably a 5- or 6-membered ring. For the substituents the preferences mentioned hereinbefore apply. As condensed alkylene, $R_1$ and $R_2$ together or $R_1$ and $R_3$ together are preferably alkylene condensed with benzene or pyridine. Examples of alkylene are: ethylene, 1,2- or 1,3-propylene, 1,2-, 1,3- or 1,4-butylene, 1,5-pentylene and 1,6-hexylene. Examples of interrupted or =O-substituted alkylene are 2-oxa-1,3-propylene, 2-oxa-1,4-butylene, 2-oxa- or 3-oxa-1,5-pentylene, 3-thia-1,5-pentylene, 2-thia-1,4-butylene, 2-thia-1,3-propylene, 2-methylimino-1,3-propylene, 2-ethylimino-1,4-butylene, 2- or 3-methylimino-1,5-pentylene, 1-oxo-2-oxa-1,3-propylene, 1-oxo-2-oxa-1,4-butylene, 2-oxo-3- 1,4-butylene and 1-oxa-2-oxo-1,5-pentylene. Examples of condensed alkylene are:

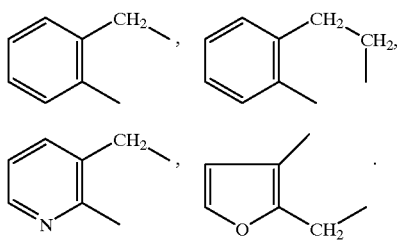

Examples of condensed and interrupted and unsubstituted or =O-substituted alkylene are:

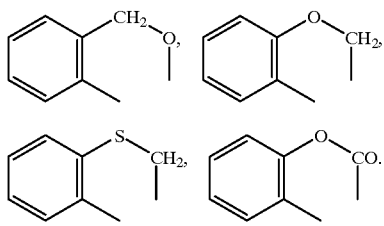

$R_4$ and $R_5$ are preferably each independently of the other hydrogen, $C_1$–$C_4$alkyl, phenyl or benzyl. $R_6$ is preferably hydrogen or $C_1$–$C_4$alkyl.

A further preferred group is formed by prochiral imines in which in formula II $R_1$, $R_2$ and $R_3$ are each different from the others and are not hydrogen.

In an especially preferred group, in formula II $R_3$ is 2,6-di-$C_1$–$C_4$alkylphen-1-yl and especially 2,6-dimethylphen-1-yl or 2-methyl-6-ethylphen-1-yl, $R_1$ is $C_1$–$C_4$alkyl and especially ethyl or methyl, and $R_2$ is $C_1$–$C_4$alkyl, $C_1$–$C_4$alkoxymethyl or $C_1$–$C_4$alkoxyethyl, and especially methoxymethyl.

Of those compounds, imines of formulae Va and Vb

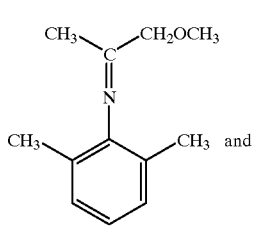

-continued

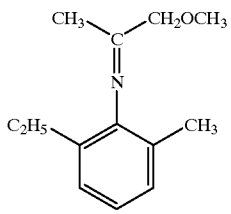

are especially important, as is the imine of formula Vc

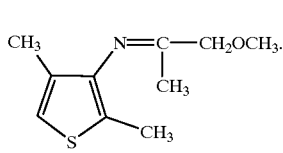

Imines of formula I are known or they can be prepared in accordance with known processes from aldehydes or ketones and primary amines.

The iridium catalysts can be added to the reaction mixture as isolated compounds. It has proved advantageous, however, to prepare the catalysts in situ with or without a solvent prior to the reaction and at the same time optionally to add some or all of the acid and of an ammonium or metal halide.

The molar ratio of imine to iridium catalyst may be, for example, from 5 000 000 to 10, especially from 2 000 000 to 20, more preferably from 1 000 000 to 100, and more especially from 1 000 000 to 1000.

The process is carried out preferably at a temperature of from −20 to 1 00° C., especially from 0 to 80° C. and more especially from 10 to 70° C., and preferably at a hydrogen pressure of from $2 \times 10^5$ to $1.5 \times 10^7$ Pa (from 5 to 150 bar), especially from $10^6$ to $10^7$ Pa (from 10 to 100 bar).

It has also been found, surprisingly, that by adding soluble ammonium or metal halides it is possible to increase both the chemical conversion, or reactivity, and the optical yield. Accordingly, a preferred form of the invention comprises the additional concomitant use of a soluble ammonium or soluble metal chloride, bromide or iodide. The chlorides, bromides and iodides are used preferably in amounts of from 0.01 to 200 equivalents, especially from 0.05 to 100 equivalents and more especially from 0.5 to 50 equivalents, based on the iridium catalyst. The iodides are preferred. Ammonium is preferably tetra-alkylammonium having from 1 to 6 carbon atoms in the alkyl groups, and the metal is preferably sodium, lithium or potassium. Special preference is given to tetrabutylammonium iodide, sodium iodide and potassium iodide. Provided that they are soluble in the reaction mixture and provided that oxidation reactions with other reactants can be ruled out, virtually any metal chlorides, bromides and iodides, that is to say those of the main groups and subgroups of the Periodic Table of the Elements, can be used in the process according to the invention.

The chlorides, bromides and iodides employed are preferably used in concentrations of from 0.01 to 500 mmol/l, especially from 0.01 to 50 mmol/l, based on the volume of the reaction mixture. When hydrohalic acids, especially HI, in the form of solid acids are used, the addition of the halide is not necessary, since an ammonium salt forms in situ with the amine that is formed.

From the Applicant's own investigations it is known that the iridium catalysts become deactivated to a greater or lesser extent during the hydrogenation depending on the reaction conditions, which leads to relatively long reaction times or requires the addition of further catalyst during the reaction in order to achieve shorter reaction times. Surprisingly, it has also been found that those disadvantages can be eliminated if an acid is added in addition to the soluble halide. The catalyst activity is increased considerably as a result. At the same time, deactivation is considerably reduced or even completely eliminated. Furthermore, the enantiomeric selectivity is, surprisingly, increased further, and optical yields of over 70% ee can be obtained even at temperatures of 50° C. and above. Accordingly, a preferred form of the process according to the invention comprises carrying out the hydrogenation in the presence of a soluble halide and additionally of an acid.

The acid is preferably used in at least the same molar amount as the iridium catalyst (equivalent to catalytic amounts) and can also be used in an amount that exceeds or is less than the molar amount. The excess may even consist in the use of the acid as solvent. In many cases it can be advantageous to use anhydrous acids. The molar ratio of imine to acid is, for example, from 1 000 000 to 100, preferably from 500 000 to 500, especially from 10 00 to 1000.

The acids may be, for example, inorganic or organic acids, inorganic or organic acidic ion exchangers, or other solid acids.

It is also to be noted that when hydrohalic acid, especially HI, is used, the addition of a soluble halide is not necessary, since the resulting amine forms soluble ammonium halides with those acids in situ.

Some examples of inorganic acids are $H_2SO_4$, highly concentrated sulfuric acid (oleum), $H_3PO_4$, orthophosphoric acid, HF, HCl, HBr, HI, $HClO_4$, $HBF_4$, $HPF_6$, $HAsF_6$, $HSbCl_6$, $HSbF_6$ and $HB(phenyl)_4$. Special preference is given to $H_2SO_4$.

Examples of organic acids are aliphatic and aromatic, optionally halogenated (fluorinated or chlorinated) carboxylic acids, sulfonic acids, phosphorus(V) acids (for example phosphonic acids or phosphonous acids) having preferably from 1 to 20, especially from 1 to 12 and more especially from 1 to 8 carbon atoms, for example formic acid, acetic acid, propionic acid, butyric acid, benzoic acid, phenylacetic acid, cyclohexanecarboxylic acid, mono-, di- and tri-chloroacetic acid, mono-, di- and tri-fluoroacetic acid, chlorobenzoic acid, methanesulfonic acid, ethanesulfonic acid, benzenesulfonic acid, p-toluenesulfonic acid, chlorobenzenesulfonic acid, trifluoromethanesulfonic acid, methylphosphonic acid and phenylphosphonic acid. Preferred acids are halogenated acids, especially $CF_3COOH$.

In another form, the acids may be inorganic or organic ion exchangers. Those materials are described frequently in the literature. Examples of inorganic ion exchangers are zeolites, clays and silica gels. Organic ion exchangers are, for example, polymers having acid groups bonded direcdy or via a bridge group, for example —COOH, —$SO_3H$ or —$PO_3H$. An example thereof are the Nafion® polymers.

In a further form, the acids may be solid acids. Within the scope of the invention, solid acids are understood to be acids that are insoluble or only swellable in the reaction medium. Within the scope of the invention a solid acid is understood to be a solid, finely divided and optionally porous material of which 1 g in 100 ml of water gives a pH value of $\leq 5$, preferably $\leq 4$ and especially $\leq 3$.

In one form, the solid acids may be metal oxide systems in gel form (sol/gel systems), for example $SiO_2$, $GeO_2$, $B_2O_3$, $Al_2O_3$, $TiO_2$, $ZrO_2$ and combinations thereof. If the extent of the desired effects is not as expected, a considerable improvement can be achieved by treating the sol/gel systems with an acid, preferably an at least dibasic acid, for example $H_2SO_4$, $H_3PO_4$ or orthophosphoric acid. Other suitable acids are, for example, HCl, HBr, HI, $HClO_4$, $HBF_4$, $HPF_6$, $HAsF_6$, $HSbCl_6$, $HSbF_6$ and $HB(phenyl)_4$, aliphatic and aromatic, optionally halogenated (fluorinated or chlorinated) carboxylic acids, sulfonic acids, phosphorus(V) acids (for example phosphonic acids or phosphonous acids) having preferably from 1 to 20, especially from 1 to 12 and more especially from 1 to 8 carbon atoms, for example formic acid, acetic acid, propionic acid, butyric acid, benzoic acid, phenylacetic acid, cyclohexanecarboxylic acid, mono-, di- and tri-chloroacetic acid, mono-, di- and tri-fluoroacetic acid, chlorobenzoic acid, methanesulfonic acid, ethanesulfonic acid, benzenesulfonic acid, p-toluenesulfonic acid, chiorobenzenesulfonic acid, trifluoromethanesulfonic acid, methyiphosphonic acid and phenyiphosphonic acid. $H_2SO_4$ is preferred.

In a further form, the acids may be inorganic or organic ion exchangers that have been treated with an at least dibasic acid, for example $H_2SO_4$, $H_2S_2O_7$ or $H_3PO_4$. Ion exchangers are known to the person skilled in the art and are described, for example, in Ullmann's Enzyklopäidie der Chemischen Technik, Vol. 13, 4th edition, pages 281 to 284. Of the organic ion exchangers special mention may be made of polymer s having acidic groups, for example —C(O)OH, —$SO_3H$ or —$PO_3H$ (for example Nafion®), which are commercially available. Of the inorganic ion exchangers special mention is to be made of natural and synthetic aluminosilicates, for example zeolites, which are described in Studies in Surface Science and Catalysis, Elsevier 1991, Vol. 58, Chapter 2, pages 13 to 33. They are commercially available. Some examples are zeolite ZSM-5, zeolite Y and mordenite.

In another form, the acids may be acidic natural or synthetic silicate minerals that have no or only limited ion exchange properties. Examples are phyllosilicates and clays, for example montmorillonite, hectorite, vermiculite, kaolinite and illite. The silicates and clays may additionally be impregnated with an acid, preferably an at least dibasic acid, for example $H_2SO_4$, $H_2SO_7$ and $H_3PO_4$, which may further increase the activity. Other suitable acids have been mentioned hereinbefore.

In a further form, the solid acids may be hetero polyacids, which preferably consist of the elements Mo, V, W, O and H as well as B, Si or P as subsidiary or trace elements. Such hetero polyacids are known and are described, for example, in Chemtech, page 23ff (November 1993) or Russian Chemicals Reviews, page 811ff (1987). Some examples are $H_3PW_{12}O_{40}$, $H_9PV_6Mo_6O_{40}$, $H_4SiMo_{12}O_{40}$ and $H_5BW_{12}O_{40}$.

Another suitable form of the solid acids comprises non-acidic, solid, finely divided and optionally porous carrier materials impregnated with an acid. Suitable carrier materials are, for example, organic polymers, such as epoxy resins, urea/aldehyde resins, melamine/aldehyde resins, polystyrene, ABS and polyolefins. Suitable inorganic carrier materials are, for example, metal and semimetal oxides ($B_2O_3$, $Al_2O_3$, $SiO_2$, $TiO_2$, $Zro_2$), metal nitrides, metal carbides, minerals such as silicates, and crushed stone. Of course, the acids must not react with the carrier materials. Suitable acids have been mentioned hereinbefore.

The reaction can be carried out in the absence or in the presence of solvents. Suitable solvents, which can be used alone or as a mixture of solvents, are, for example:

aliphatic and aromatic hydrocarbons, for example pentane, hexane, cyclohexane, methylcyclohexane, benzene, toluene and xylene; ethers, for example diethyl ether, diethylene glycol dimethyl ether, tetrahydrofuran and dioxane; halogenated hydrocarbons, for example methylene chloride, chloroform, 1,1,2,2-tetrachloroethane and chlorobenzene; esters and lactones, for example ethyl acetate, butyrolactone and valerolactone; acid amides and lactams, for example dimethylformamide, dimethylacetamide and N-methylpyrrolidone, and ketones, for example acetone, dibutyl ketone, methyl isobutyl ketone and methoxyacetone.

In detail, the process according to the invention can be carried out by first preparing the catalyst by dissolving, for example, (Ir-dieneCl)$_2$ and a diphosphine in a solvent or in a portion of the substance to be hydrogenated; there are then added the solid acid, directly or in the form of a slurry in a solvent, and the imine (where appropriate in the form of a solution). The mixture is hydrogenated in an autoclave and the reaction mixture is isolated and purified in a manner known per se, for example by precipitation, extraction or distillation. It has proved advantageous to use as the initial batch the solid acid together with the components required for formation of the catalyst and, where appropriate, a solvent, then to add the imine and to form the catalyst in situ in the initial phase of the hydrogenation.

Prior to the hydrogenation, the reaction is advantageously carried out under a protective gas. It is advantageous to ensure that the catalyst solution stands for only a short time and to carry out the hydrogenation of the imines as soon as possible following preparation of the catalyst solution.

In the case of the hydrogenation of aldimines and ketimines, the aldimines and ketimines can also be formed in situ before or during the hydrogenation. In a preferred form, an amine and an aldehyde or a ketone are mixed together and added to the catalyst solution and the aldimine or ketimine formed in situ is hydrogenated. It is also possible, however, to use an amine, a ketone or an aldehyde together with the catalyst as the initial batch and to add the ketone or the aldehyde or the amine thereto, either all at once or in metered amounts.

The hydrogenation can be carried out continuously or batchwise in various types of reactor. Preference is given to those reactors which allow comparatively good intermixing and good removal of heat, such as, for example, loop reactors. That type of reactor has proved to be especially satisfactory when small amounts of catalyst are used.

The process according to the invention yields the corresponding amines in short reaction times while having chemically a high degree of conversion, with surprisingly good optical yields (ee) of 70% or more being obtained even at relatively high temperatures of more than 50° C., and even with high molar ratios of imine to catalyst.

The hydrogenated organic compounds that can be prepared in accordance with the invention, for example the amines, are biologically active substances or are intermediates for the preparation of such substances, especially in the field of the preparation of pharmaceuticals and agrochemicals. For example, o,o-dialkylarylketamine derivatives, especially those having alkyl and/or alkoxyalkyl groups, are effective as fungicides, especially as herbicides. The derivatives may be amine salts, acid amides, for example of chloroacetic acid, tertiary amines and ammonium salts (see, for example, EP-A-0 077 755 and EP-A-0 115 470).

Especially important in this connection are the optically active amines of formula VI

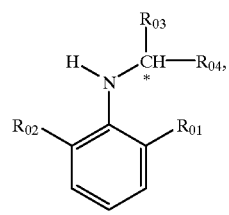

(VI)

which can be prepared using the processes according to the invention from the imines of formula (V) in the presence of asymmetric iridium catalysts, and wherein $R_{01}$, $R_{02}$ and $R_{03}$ are each independently of the others $C_1$–$C_4$alkyl, and $R_{04}$ is $C_1$–$C_4$alkyl or $C_1$–$C_4$alkoxymethyl or $C_1$–$C_4$alkoxyethyl, and especially the amines of formulae

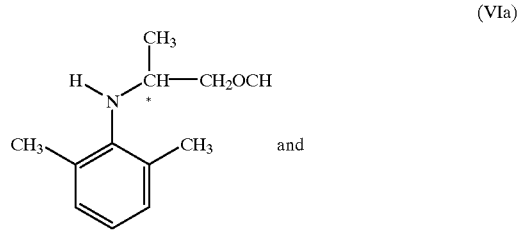

(VIa)

and

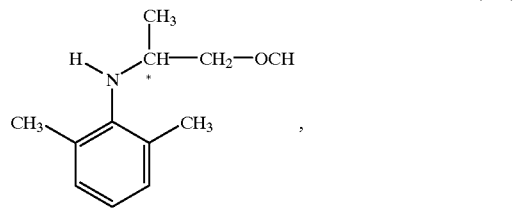

(VIb)

which can be prepared from the imines of formulae (Va) and (Vb) and which can be converted in accordance with methods that are customary per se with chloroacetic acid into the desired herbicides of the chloroacetanilide type; of those amines, very special preference is given to those compounds that have the S configuration at the asymmetric C* atom.

The invention relates also to the use of the compounds of formulae I, Ia and Ib in the hydrogenation, especially the enantioselective hydrogenation, of imines.

The Examples that follow illustrate the invention in more detail. The chemical conversion is determined by gas chromatography (2 m OV 101 column/100 to 200° C. at 10° C./min.). The optical yields (enantiomeric excess, ee) are determined either by gas chromatography [Chirasil-Val column, 50 m, manufacturer Ailtech, USA, T=150° C., isothermic], by HPLC (Chiracel OD column) or by $^1$H-NMR spectroscopy (using shift reagents).

The following abbreviations are used for the diphosphines:

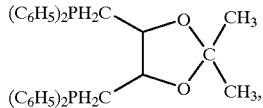

(DIOP)

-continued

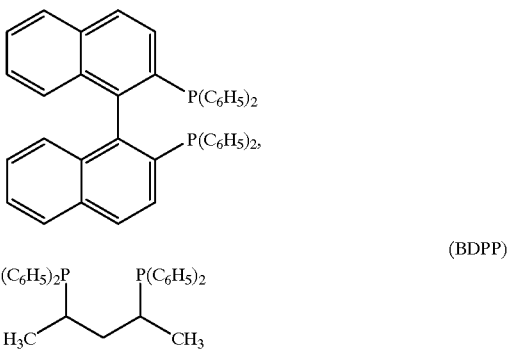

(BINAP)

(BDPP)

{(R)-1-[(S)-2-(diphenylphosphino)ferrocenyl]}ethyl-bis[(3,5-dimethyl)phenyl]phosphine [PPF-P(xyl)$_2$]

{(R)-1-[(S)-2-(diphenylphosphino)ferrocenyl]}ethyl-bis[(3,5-dimethyl-4-dimethylamino)-phenyl]phosphine [PPF-P(NMe$_2$xyl)$_2$]

{(R)-1-[(S)-2-(diphenylphosphino)ferrocenyl]}ethyl-di-(tert-butyl)phosphine [PPF-P(t-BU)$_2$]

The dimeric starting materials [Ir(diphosphine)HI$_2$]$_2$ are prepared in accordance with the Examples of EP-A-0 612 758.

A) PREPARATION EXAMPLES

Example A1

Preparation of Ir(DIOP)(CH$_3$CO$_2$)HI 0.2 g (0.11 mmol) of [Ir(DIOP)HI$_2$]$_2$ is dissolved in 10 ml of methylene chloride at 25° C. in the presence of 0.04 g of silver acetate, and stirring is then carried out for one hour. The resulting silver iodide is then filtered off over Celite and the filtrate is concentrated to 1 ml. After the addition of 10 ml of diethyl ether, a yellow precipitate forms, which is isolated by filtration, washed three times with 5 ml of diethyl ether and then dried in vacuo. 145 mg (75% yield) of the title compound are obtained.

$^1$H-NMR (220 MHz, CD$_2$Cl$_2$): hydride region, −15.6 (t, J=16 Hz, 25%), −26.9 (dd, ΣJ=41 Hz, 10%), −27.3 (dd, ΣJ=42 Hz, 65%).

Elemental analysis % found (calculated): C: 44.59 (45.16); H: 4.05 (4.13); P: 6.98 (7.06); I: 14.30 (14.46).

Example A2

Preparation of Ir(BINAP)(2,4,6-trimethylphenylCO$_2$)HI 90 mg (0.042 mmol) of [Ir(BINAP)HI$_2$]$_2$ are dissolved in 5 ml of methylene chloride at 25° C. in the presence of 25 mg (0.092 mmol) of silver 2,4,6-trimethylbenzoate, and stirring is then carried out for 2 hours. The resulting silver iodide is then filtered off over Celite and the filtrate is concentrated to 1 ml. After the addition of 10 ml of pentane, a red-orange precipitate forms, which is isolated by filtration, washed three times with 5 ml of pentane and then dried in vacuo. 43 mg (46% yield) of the title compound are obtained.

$^1$H-NMR (220 MHz, CD$_2$Cl$_2$): 1.89 (s, 6H, 2 ortho-CH$_3$), 2.14 (s, 3H, 1-para-CH$_3$); hydride region: −26.0 (dd, ΣJ=39 Hz).

Elemental analysis % found (calculated): C: 58.70 (58.64); H: 3.97 (4.01); P: 5.47 (5.60); I: 11.53 (11.47).

Example A3

Preparation of Ir(BINAP)(2,4,6-trimethylphenylCO$_2$)$_2$H 100 mg (0.047 mmol) of [Ir(BINAP)HI$_2$]$_2$ are dissolved in 25 ml of methylene chloride at 25° C. in the presence of 28 mg (0.01 mmol) of silver 2,4,6-trimethylbenzoate, and stirring is then carried out for 5 hours. The resulting silver iodide is then filtered off over Celite and the filtrate is concentrated to dryness. A yellow-green solid is obtained, which is washed twice with 5 ml of diethyl ether and twice with 5 ml of pentane and is then dried in vacuo. The title compound is obtained in a yield of 70%.

$^1$H-NMR (220 MHz, CD$_2$Cl$_2$): 1.49 (s, 3H, 3 para-CH$_3$), 1.65 (s, 3H, 1-para-CH$_3$); 2.13 (s, 3H, 1-ortho-CH$_3$); 2.23 (s, very broad, 9H, 3 ortho-CH$_3$); hydride region: −24.5 (dd, ΣJ=44 Hz).

Elemental analysis % found (calculated): C: 67.11 (67.35); H: 4.98 (4.77); P: 5.13 (5.43).

Example A4

Preparation of Ir(DIOP)(CH$_3$CO$_2$)$_3$ 15 equivalents (550 mg) of silver acetate are added at 25° C. to a solution of 200 mg (0.11 mmol) of [Ir(DIOP)HI$_2$]$_2$ in 20 ml of methylene chloride. The mixture is stirred for 12 hours and is filtered over Celite. The filtrate is concentrated to 2 ml, and 20 ml of pentane are added slowly. The mixture is left to stand overnight, is filtered and is dried in vacuo. 135 mg (yield 70%) of the title compound are obtained in the form of yellow crystals.

$^1$H-NMR (220 MHz, CD$_2$Cl$_2$): 1.50 (s, 6H, 2 CH$_3$); 2.24 (s, 3H, 1 CH$_3$).

Elemental analysis % found (calculated): C: 50.52 (51.21); H: 4.89 (4.76); P: 6.99 (7.14).

Example A5

Preparation of Ir(BINAP)(CF$_3$CO$_2$)$_3$ 400 mg (1.81 mmol) of silver acetate are added at 25° C. to a solution of 200 mg (0.093 mmol) of [Ir(BINAP)HI$_2$]$_2$ in 15 ml of methylene chloride. The mixture is stirred for 24 hours and filtered over Celite. The filtrate is concentrated to dryness in vacuo and the brown residue is dissolved in 20 ml of diethyl ether. The mixture is filtered again and concentrated to 2 ml. After the addition of 15 ml of pentane, a reddish brown precipitate forms, which is isolated by filtration, washed three times with 10 ml of pentane and then dried in vacuo. 130 mg (yield 60%) of the title compound are obtained in the form of a mixture of position isomers.

$^{31}$P{$^1$H}-NMR (81 MHz, CD$_2$Cl$_2$/CH$_2$Cl$_2$): −24.1 and −26.8 (AX, $^2$J$_{pp}$=21 Hz, 85–100%, main fraction); −25.1 and −28.4 (AX, $^2$J$_{pp}$=21 Hz, 15–0%, secondary fraction).

Elemental analysis % found (calculated): C: 49.39 (52.04); H: 3.00 (2.80); P: 4.48 (5.37); F: 12.97 (14.82).

Example A6

Preparation of Ir(BDPP)(CF$_3$CO$_2$)$_3$ 100 mg (0.056 mmol) of [Ir(BDPP)HI$_2$]$_2$ and 250 mg (1.13 mmol) silver acetate are weighed into a 50 ml flask under an N$_2$ atmosphere, and 15 ml of toluene are added. The mixture is stirred at 25° C. for 15 hours, the precipitate is filtered off, and the filtrate is concentrated to dryness by evaporation in a rotary evaporator. The reddish brown residue is dissolved in 4 ml of chloroform, filtered and concentrated to dryness in vacuo. The brown-beige residue is dissolved in 10 ml of diethyl ether and is again filtered and concentrated to dryness, and the beige solid is washed with pentane. Yield: 80 mg (75%). Recrystallisation from toluene/pentane yields yellowish orange crystals.

$^{31}$P{$^1$H}-NMR (121 MHz, CDCl$_3$): −15.6 and −21.2 (AX, $^2$J$_{pp}$=21 Hz). Elemental analysis % found (calculated): C: 42.18 (43.26); H: 3.34 (3.11); P: 6.21 (6.37); F: 15.77 (17.60).

Example A7
Preparation of Ir[PPF-P(xyl)$_2$](CF$_3$CO$_2$)$_3$ 100 mg (0.046 mmol) of [Ir(PPF-P(xyl)$_2$HI$_2$]$_2$ and 200 mg of AgCF$_3$CO$_2$ (20 equivalents) are mixed with 20 ml of toluene and 2 ml of methylene chloride, and stirring is carried out for 12 hours. The mixture is then filtered over Celite and concentrated to dryness in vacuo. The brown residue is dissolved in 5 ml of chloroform and is again filtered, concentrated and concentrated to dryness by evaporation, and the procedure is repeated once more. The residue is taken up in 3 ml of chloroform, and 20 ml of pentane are added. The brown precipitate is isolated by filtration, washed twice with 10 ml of pentane and dried in vacuo. Yield: 85 mg (79%).

$^{31}$P{$^1$H}-MR (121 MHz, CDCl$_3$): −1.0 and −25.1 (AX, $^2J_{pp}$=22.5 and 22.6 Hz, 55%); −8.3 and −25.1 (AX, $^2J_{pp}$=24.0 and 23.4 Hz, 45%).

Example A8
Preparation of Ir[PPF-P(xyl)$_2$](CH$_3$CO$_2$)$_3$

Example A6 is repeated using silver acetate. A brown solid is obtained in a yield of 81%.

$^{31}$P{$^1$H}-NMR (121 MHz, CDCl$_3$): −8.9 and −20.5 (AX, $^2J_{pp}$=25.0 and 24.9 Hz, 52%); −5.9 and −22.3 (AX, $^2J_{pp}$=23.7 and 24.0 Hz, 13%); −2.4 and −23.7 (AX, $^2J_{pp}$=24.8 and 24.3 Hz, 11%); −5.1 and −26.7 (AX, $^2J_{pp}$=24.4 and 24.3 Hz, 9%).

Example A9
Preparation of Ir[PPF-P(xyl)$_2$](C$_6$F$_5$CO$_2$)$_3$

Example A6 is repeated using silver pentafluorobenzoate. A dark-brown solid is obtained in a yield of 86%.

$^{31}$P{$^1$H}-NMR (121 MHz, CDCl$_3$): −2.9 and −25.9 (AX, $^2J_{pp}$=24.3 and 24.7 Hz, 38%); −2.1 and −27.1 (AX, $^2J_{pp}$=22.8 and 23.2 Hz, 23%); −1.6 and −22.4 (AX, $^2J_{pp}$=23.1 Hz, 13%); −2.0 and −24.3 (AX, $^2J_{pp}$=19.1 Hz, 19%); −6.3 and −22.3 (AX, 5%); −10.9 and −24.3 (AX, 3%);

Example A10
Preparation of Ir[PPF-P(t-Bu)$_2$](CF$_3$CO$_2$)$_3$

A mixture of 80 mg (0.04 mmol) of [Ir(PPF-(t-Bu)$_2$)HI$_2$]$_2$, 180 mg (0.82 mmol) of AgCF$_3$CO$_2$, 10 ml of toluene and 4 ml of methylene chloride is stirred overnight. The mixture is filtered over Celite and concentrated to dryness by evaporation. The brown residue is dissolved in 4 ml of chloroform, filtered and concentrated to dryness by evaporation, and the procedure is repeated. The brown residue is taken up in 15 ml of diethyl ether, filtered again and then concentrated to 2 ml. After the addition of 15 ml of pentane, a brown precipitate forms, which is washed twice with 10 ml of pentane and then dried in vacuo. Brown solid in a yield of 71%.

$^{31}$P{$^1$H}-NMR (121 MHz, CDCl$_3$): −7.9 and −15.4 (AX, $^2J_{pp}$=18.8 and 18.5 Hz, 70%); −9.5 and −24.1 (m, 30%).

Example A11
Preparation of Ir[PPF-P(t-Bu)$_2$](CH$_3$CO$_2$)$_3$ 200 mg (0.04 mmol) of silver acetate are added to a solution of 80 mg (0.04 mmol) of [Ir(PPF-(t-Bu)$_2$)HI$_2$]$_2$ in 10 ml of methylene chloride, and the mixture is stirred for 24 hours. It is then filtered over Celite and concentrated to dryness by evaporation. The solid residue is taken up in 30 ml of diethyl ether, filtered over Celite and concentrated to 4 ml. After the addition of 15 ml of pentane, a black precipitate forms, which is washed twice with 10 ml of pentane. 50 mg (69%) of a black solid are obtained.

$^{31}$P{$^1$H}-NMR (121 MHz, CDCl$_3$):
23.5 and −24.2 (AX, $^2J_{pp}$=24.2 and 24.5 Hz, 67%); 22.1 and −31.3 (AX, $^2J_{pp}$=22.8 and 23.2 Hz, 11%); −8.1 (d, $^2J_{pp}$=20.6 Hz); −9.0 (d, 3%); −11.9 (m, 10%); −13.8 (d, $^2J_{pp}$=20.3 Hz, 3%).

Example A12
Preparation of Ir[PPF-P(t-Bu)$_2$](C$_6$F$_5$CO$_2$)$_3$

Example A10 is repeated using silver pentafluorobenzoate. A brown solid is obtained in a yield of 52%.

$^{31}$P{$^1$H}-NMR (121 MHz, CDCl$_3$): −7.5 (broad m) and −15.1 (broad m, 75%); −6.0 and −12.1 (broad m, 25%).

APPLICATION EXAMPLES

For the imines that are used, the following abbreviations apply:

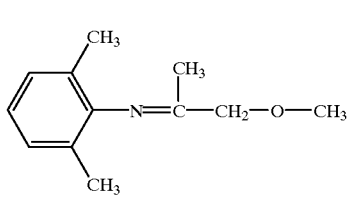
DMA

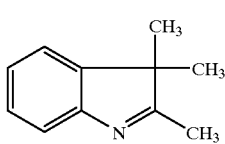
TMI

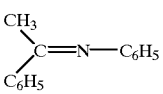
API

Examples B1–B9
Hydrogenation of imines using Ir(DIP)(RCO$_2$)HI

In a 50 ml steel autoclave, the catalyst (0.0157 mmol) is dissolved in 2.5 ml of methylene chloride and 7.5 ml of tetrahydrofuran. The imine (7.83 mmol, 500 equivalents) is added to the solution. The autoclave is degassed three times with hydrogen at 25 bar. Then it is heated to 30° C. and 40 bar hydrogen is pressed on. In order to study the progress of the reaction, samples may be taken periodically via a built-in cannula. The results are given in Table 1 below. $t_{1/2}$ is the time to 50% conversion and t is the total reaction time.

TABLE 1

| No. | DIP | R | Imine | t½(h) | t(h) | Yield (%) | Optical yield (% ee) |
|---|---|---|---|---|---|---|---|
| 1 | (+)-DIOP | CH$_3$ | DMA | 1 | 4 | 99 | 41(S) |
| 2 | (+)-DIOP | CH$_3$ | TMI | 2.5 | 24 | 99 | 30(−) |
| 3 | (−)-DIOP | CF$_3$ | TMI | 9 | 29 | 98 | 36(+) |
| 4 | (−)-DIOP | Mes* | TMI | 6 | 25 | 92 | 52(+) |
| 5 | (+)-BINAP | CH$_3$ | DMA | 35 | 197 | 98 | 29(S) |
| 6 | (+)-BINAP | CF$_3$ | DMA | — | 48 | 4 | not determined |
| 7 | (+)-BINAP | Mes* | DMA | 72 | 283 | 79 | 17(S) |
| 8 | (−)-BDPP | CF$_3$ | DMA | 16 | 71 | 88 | 74(R) |
| 9 | (−)-BDPP | CF$_3$ | TMI | 38 | 63 | 79 | 57(+) |

*Mes is mesityl

Examples B10–B15
Hydrogenation of imines using Ir(DIP)(RCO$_2$)$_2$H

The procedure of Example B1 is followed. The results are given in Table 2. The molar ratio of imine to catalyst is 500 in Examples B10–B12 and B15 and 200 in Examples 13 14.

TABLE 2

| No. | DIP | R | Imine | t½(h) | t(h) | Yield (%) | Optical yield (% ee) |
|---|---|---|---|---|---|---|---|
| 10 | (−)-DIOP | $CH_3$ | TMI | 45 | 140 | 85 | 33(+) |
| 11 | (−)-DIOP | $CF_3$ | TMI | 20 | 69 | 96 | 23(+) |
| 12 | (+)-DIOP | $CH_3$ | DMA | 64 | 233 | 75 | 29(S) |
| 13 | (+)-BINAP | Mes | DMA | — | 67 | 3 | not determined |
| 14 | (+)-BINAP | $CH_3$ | DMA | 110 | 188 | 57 | 2(S) |
| 15 | (+)-BINAP | ** | DMA | 8 | 42 | 92 | 31(S) |

** $SO_3$—$CF_3$

Examples B16–B25
Hydrogenation of DMA using $Ir(DIP)(RCO_2)_3$

The procedure of Example B1 is followed. In Examples B17, B20 and B23, the molar ratio of DMA to catalyst is 200; otherwise it is 500. The results are given in Table 3.

TABLE 3

| No. | DIP | R | Imine | t½(h) | t(h) | Yield (%) | Optical yield (% ee) |
|---|---|---|---|---|---|---|---|
| 16 | (−)-DIOP | $CH_3$ | DMA | 16 | 80 | 98 | 31(R) |
| 17 | (+)-DIOP | $CF_3$ | DMA | 4 | 11 | 100 | 7(S) |
| 18 | (+)-DIOP | $C_6F_5$ | DMA | — | 38 | 96 | 32(S) |
| 19 | (+)-DIOP | $C_6H_6$ | DMA | — | 55 | 87 | 15(S) |
| 20 | (+)-BINAP | $CH_3$ | DMA | — | 19 | 29 | 56(S) |
| 21 | (+)-BINAP | $CF_3$ | DMA | 2.5 | 8.5 | 100 | 67(S) |
| 22 | (+)-BINAP | $C_6F_5$ | DMA | 1 | 5 | 100 | 17(S) |
| 23 | (−)-BDPP | $CH_3$ | DMA | — | 42 | 65 | 82(R) |
| 24 | (−)-BDPP | $CF_3$ | DMA | 3.5 | 10 | 100 | 84(R) |
| 25 | (−)-BDPP | $C_6F_5$ | DMA | 8 | 27 | 92 | 60(R) |

Examples B26–B31
Hydrogenation of other imines using $Ir(DIP)(RCO_2)_3$

The procedure of Example B1 is followed. In Examples B26, B27, B28, B29 and B31, the molar ratio of imine to catalyst is 200; otherwise it is 500. The results are given in Table 4. In Example 31, 10 ml of tetrahydrofuran are used as solvent.

TABLE 4

| No. | DIP | R | Imine | t½(h) | t(h) | Yield (%) | Optical yield (% ee) |
|---|---|---|---|---|---|---|---|
| 26 | (+)-DIOP | $CH_3$ | TMI | 20 | 70 | 90 | 35(−) |
| 27 | (+)-DIOP | $CF_3$ | TMI | 22 | 51 | 100 | 31(−) |
| 28 | (+)-BINAP | $CF_3$ | TMI | 43 | 79 | 86 | 31(−) |
| 29 | (+)-BINAP | $CF_3$ | API | 16 | 38 | 95 | 60(R) |
| 30 | (−)-BDPP | $CF_3$ | API | 32 | 170 | 97 | 33(S) |
| 31 | (−)-BDPP | $CF_3$ | TMI | 1.5 | 4 | 99 | 64(+) |

Exaples B32–B38
Temperature-dependence of DMA hydrogenation using $Ir(IP)(RCO_2)_3$ The procedure of Example B1 is followed, but at different temperatures. The results are given in Table 5.

TABLE 5

| No. | DIP | R | T(° C.) | t½(h) | t(h) | Yield (%) | Optical yield (% ee) |
|---|---|---|---|---|---|---|---|
| 32 | (+)-BINAP | $CF_3$ | 0 | 20 | 60 | 97 | 77(S) |
| 33 | (+)-BINAP | $CF_3$ | 30 | 2.5 | 8.5 | 100 | 67(S) |
| 34 | (+)-BINAP | $CF_3$ | 50 | 0.4 | 1.7 | 100 | 59(S) |
| 35 | (+)-DIOP | $CF_3$ | 30 | 4 | 11 | 100 | 7(S) |
| 36 | (+)-DIOP | $CF_3$ | 80 | 0.8 | 2 | 100 | 7(S) |
| 37 | (−)-BDPP | $CF_3$ | 0 | 50 | 145 | 96 | 90(R) |
| 38 | (−)-BDPP | $CF_3$ | 30 | 3.5 | 10 | 100 | 84(R) |

Examples 39–48

Hydrogenation of DMA using $Ir(DIP)(RCO_2)_3$ in different solvents Example B1 is repeated using different solvents. The results are shown in Table 6.

TABLE 6

| No. | DIP | R | Solvent | t½(h) | t(h) | Yield (%) | Optical yield (% ee) |
|---|---|---|---|---|---|---|---|
| 39 | (+)-BINAP | $CF_3$ | aa | 2.5 | 8.5 | 100 | 67(S) |
| 40 | (+)-BINAP | $CF_3$ | bb | 2.5 | 8.5 | 100 | 57(S) |
| 41 | (+)-BINAP | $CF_3$ | cc | 1.2 | 4 | 100 | 70(S) |
| 42 | (+)-BINAP | $CF_3$ | dd | 6 | 17 | 100 | 73(S) |
| 43 | (+)-BINAP | $CF_3$ | ee | 2.5 | 11 | 99 | 64(S) |
| 44 | (+)-BINAP | $CF_3$ | ff | 8 | 14 | 54[1] | 60(S) |
| 45 | (−)-BDPP | $CH_3$ | aa | — | 42 | 65 | 82(R) |
| 46 | (−)-BDPP | $CH_3$ | cc | — | 90 | 35 | 90(R) |
| 47 | (−)-BDDP | $CF_3$ | cc | 1.5 | 3.5 | 95 | 85(R) |
| 48 | (−)-BDPP | $CF_3$ | dd | — | 22 | 82 | 89(R)[2] |

[1] 40% of the imine is hydrolysed
[2] 0.0047 mmol of catalyst; ratio DMA:catalyst = 1500
aa = tetrahydrofuran/methylene chloride (3:1)
bb = methylene chloride
cc = tetrahydrofuran
dd = toluene
ee = methanol/benzene (1:1)
ff = tetrahydrofuran/water (10:1)

Examples B49–B52

Hydrogenation of DMA using $Ir(DIP)(RCO_2)_3$ at different hydrogen pressures

The procedure of Example B1 is followed, but the pressure is varied. The results are given in Table 7.

TABLE 7

| No. | DIP | R | $H_2$ pressure (bar) | t½(h) | t(h) | Yield (%) | Optical yield (% ee) |
|---|---|---|---|---|---|---|---|
| 49 | (+)-BINAP | $CF_3$ | 10 | 3.5 | 12 | 100 | 67(S) |
| 50 | (+)-BINAP | $CF_3$ | 20 | 3.0 | 10 | 100 | 68(S) |
| 51 | (+)-BINAP | $CF_3$ | 30 | 2.5 | 8.5 | 100 | 67(S) |
| 52 | (+)-BINAP | $CF_3$ | 40 | 0.75 | 2 | 100 | 69(S) |

Examples B53–B59

Hydrogenation of DMA using $Ir(DIP)(RCO_2)_3$ with different molar ratios of $DMA(S):Ir(DIP)(RCO_2)_3(Ir)$ (S/Ir)

The procedure of Example B1 is followed and the ratio S/Ir is varied. In Example B59, tetrahydrofuran is used as solvent. The results are given in Tables 8 and 9.

TABLE 8

(concentration of DMA constant)

| No. | DIP | R | S/Ir | t½(h) | t(h) | Yield (%) | Optical yield (% ee) |
|---|---|---|---|---|---|---|---|
| 53 | (+)-BINAP | $CF_3$ | 200 | 2 | 7.5 | 100 | 68(S) |
| 54 | (+)-BINAP | $CF_3$ | 500 | 2.5 | 8.5 | 100 | 67(S) |
| 55 | (+)-BINAP | $CF_3$ | 1000 | 3.5 | 14 | 93 | 67(S) |

TABLE 9

(concentration of Ir(DIP)(RCO$_2$)$_3$ constant)

| No. | DIP | R | S/Ir | t½(h) | t(h) | Yield (%) | Optical yield (% ee) |
|---|---|---|---|---|---|---|---|
| 56 | (+)-BINAP | $CF_3$ | 250 | 1.75 | 6 | 100 | 66(S) |
| 57 | (+)-BINAP | $CF_3$ | 500 | 2.5 | 8.5 | 100 | 67(S) |
| 58 | (+)-BINAP | $CF_3$ | 1000 | 8.5 | 19 | 100 | 67(S) |
| 59 | (+)-BINAP | $CF_3$ | 500 | 1.2 | 4 | 100 | 68(S) |
|    |           |        | 500[a)] | 2 | 6 | 100 | 68(S) |

[a)]500 equivalents added after the first hydrogenation and catalyst used again.

Examples B60–B61

Hydrogenation of DMA using Ir(DIP)(RCO$_2$)$_3$ with different molar ratios of DMA(S):Ir(DIP)(RCO$_2$)$_3$(Ir) (S/Ir)

The procedure of Example B1 is followed. The amount of Ir(DIP)(RCO$_2$)$_3$ is 0.0051 mmol. The solvent is tetrahydrofuran (20 ml) in Example B60 and toluene (10 ml) in Example B61. The results are shown in Table 10.

TABLE 10

| No. | DIP | R | S/Ir | t½(h) | t(h) | Yield (%) | Optical yield (% ee) |
|---|---|---|---|---|---|---|---|
| 60 | (−)-BDPP | $CF_3$ | 3000 | 6.5 | 11 | 96 | 85(S) |
| 61 | (−)-BDPP | $CF_3$ | 1500 | — | 22 | 82 | 89(S) |

Examples B62–B66

Hydrogenation of DMA using Ir(DIP)(RCO$_2$)$_3$ with DIP equal to ferrocenyl diphosphine ligands The procedure of Example B1 is followed, but 10 ml of THF are used as solvent. The results are summarised in Table 11.

TABLE 11

| No. | DIP | R | S/Ir | t(h) (%[1]) | t$_{end}$ (h) | Yield (%) | Optical yield (% ee) |
|---|---|---|---|---|---|---|---|
| 62 | PPF-P(xyl)$_2$ | $CF_3$ | 500 | 2(36) | 6 | 84 | 55(S) |
| 63 | PPF-P(xyl)$_2$ | $CF_3$ | 1000 | 2.5(25) | 30 | 92 | 55(S) |
| 64 | PPF-P(xyl)$_2$ | $CH_3$ | 500 | 4(76) | 7 | 100 | 72(S) |
| 65 | PPF-P(xyl)$_2$ | $C_6F_5$ | 500 | 4(29) | 21 | 79 | 55(S) |
| 66 | PPF-P(t-Bu)$_2$ | $CF_3$ | 500 | 8(10) | 66 | 21 | 39(S) |

[1])% conversion

Examples B67–B72

Hydrogenation of DMA using Ir(DIP)(CF$_3$CO$_2$)$_3$ with the addition of soluble tetrabutylammonium iodide (TBAI) as well as tetrabutylammonium iodide and trifluroacetic acid (TFE)

The reactions are carried out in a 50 ml autoclave without a solvent. The hydrogen pressure is 80 bar. 5 ml of DMA are used. In Comparison Example A and Examples B67–B69, DIP is (R)-(S)-PPF-P(xyl)$_2$. In Comparison Example B and Examples B70–B72, DIP is (2S;4S)-BDPP. Further details and the results are given in Table 12.

TABLE 12

| No. | TBAI (mg) | TFE (ml) | S/Ir | t (h) | T (° C.) | Yield (%) | Optical yield (% ee) |
|---|---|---|---|---|---|---|---|
| A | — | — | 2000 | 66 | 30 | 79 | 44.3 (S) |
| 67 | 12 | — | 2000 | 19 | 30 | 93 | 53.8 (S) |
| 68 | 12 | 0.05 | 2000 | 2.5 | 30 | 100 | 71.7 (S) |
| 69 | 12 | 0.05 | 10000 | 1.5 | 30 | 100 | 70.8 (S) |
| B | — | — | 2000 | 17.5 | 30 | 98 | 77.2 (R) |
| 70 | 12 | 0.05 | 2000 | 20 | 30 | 99.5 | 58.5 (R) |
| 71 | 12 | 0.05 | 10000 | 15 | 30 | 100 | 59.5 (R) |
| 72 | 12 | 0.05 | 20000 | 18 | 50 | 100 | 49.5 (R) |

What is claimed is:

1. A compound of formula I, Ia or Ib, or a mixture of at least two of those compounds $$(DIP)IrX_qY_r(Z) \tag{I}$$

$$(DIP)IrX_sY_t(Z)_2 \tag{Ia}$$

$$(DIP)Ir(Z)_3 \tag{Ib}$$

wherein

DIP is a ditertiary diphosphine, the two phosphine groups of which are bonded to a $C_2$-, $C_3$- or $C_4$-carbon chain, with the result that the diphosphine forms a 5- to 7-membered ring together with the Ir atom, X is Cl, Br or I, Y is a hydrogen atom, q and r are 0, 1 or 2 and the sum of q+r is 2, s and t are 0 or 1 and the sum of s+t is 1, and Z is the anion of an organic oxy acid that contains a group C(=O)O, S(=O)O or P(=O)O in the anion.

2. A compound or mixture according to claim 1 wherein, in the compounds of formulae I, Ia and Ib, DIP is a ditertiary diphosphine (a) the phosphine groups of which are bonded to different carbon atoms of a carbon chain having from 2 to 4 carbon atoms, or (b) the phosphine groups of which are either bonded directly or via a bridge group —CR$_v$R$_w$— in the ortho positions of one cyclopentadienyl ring or are bonded to each cyclopentadienyl ring of a ferrocenyl, or (c) one phosphine group of which is bonded to a carbon chain having 2 or 3 carbon atoms and the other phosphine group of which is bonded to an oxygen atom or a nitrogen atom bonded terminally to that carbon chain, or (d) the phosphine groups of which are bonded to the two oxygen atoms or nitrogen atoms bonded terminally to a $C_2$-carbon chain; with the result that in the cases of (a), (b), (c) and (d) a 5-, 6- or 7-membered ring is formed together with the Ir atom, and R$_v$ and R$_w$ are each independently of the other hydrogen, $C_1$–$C_8$alkyl, $C_1$–$C_4$fluoroalkyl, phenyl or benzyl or are phenyl or benzyl each having from 1 to 3 $C_1$–$C_4$alkyl or $C_1$–$C_4$alkoxy substituents.

3. A compound or mixture according to claim 1 wherein R$_w$ is hydrogen and R$_v$ is $C_1$–$C_4$alkyl.

4. A compound or mixture according to claim 1 wherein the diphosphine DIP contains at least one chiral group.

5. A compound or mixture according to claim 4 wherein the diphosphine is an optically pure stereoisomer.

6. A compound or mixture according to claim 4 wherein the phosphine groups contain identical or different unsubstituted or substituted hydrocarbon radicals having from 1 to 20 carbon atoms.

7. A compound or mixture according to claim 4 wherein the phosphine groups contain two identical or different radicals from the following group: linear or branched $C_1$–$C_{12}$alkyl; unsubstituted or $C_1$–$C_6$alkyl- or $C_1$–$C_6$alkoxy-substituted $C_5$–$C_{12}$cycloalkyl, $C_5$–$C_{12}$cycloalkyl-$CH_2$-, phenyl or benzyl; and phenyl or benzyl each of which is substituted by halogen, $C_1$–$C_6$haloalkyl, $(C_1$–$C_{12}$alkyl$)_3$Si, $(C_6H_5)_3$Si, $C_1$–$C_6$haloalkoxy, —$NH_2$, phenyl$_2$N—, benzyl$_2$N—, morpholinyl, piperidinyl, pyrrolidinyl, $(C_1$–$C_{12}$alkyl$)_2$N—, -ammonium-$X_1^\ominus$, —$SO_3M_1$, —$CO_2M_1$, —$PO_3M_1$ or by —COO—$C_1$–$C_6$alkyl, wherein $M_1$ is an alkali metal or hydrogen and $X_1^\ominus$ is the anion of a monobasic acid.

8. A compound or mixture according to claim 4 wherein the phosphine groups are a radical of the formula

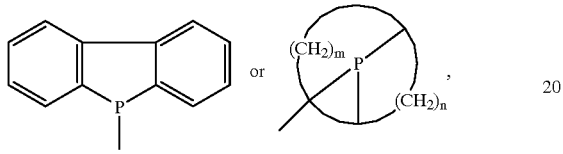

wherein m and n are each independently of the other an integer from 2 to 10, and the sum of m+n is from 4 to 12.

9. A compound or mixture according to claim 4 wherein the phosphine groups are a radical of the formula

wherein $R_{103}$ is $C_1$–$C_4$alkylene, and $R_{104}$ and $R_{105}$ are each independently of the other hydrogen, $C_1$–$C_6$alkyl, $C_1$–$C_6$alkoxy, $C_1$–$C_6$haloalkyl, $C_5$- or $C_6$-cycloalkyl, phenyl that is unsubstituted or substituted by $C_1$–$C_4$-alkyl, $C_1$–$C_4$alkoxy, $C_1$–$C_4$haloalkyl or by halogen, or benzyl that is unsubstituted or substituted by $C_1$–$C_4$alkyl, $C_1$–$C_4$alkoxy, $C_1$–$C_4$haloalkyl or by halogen.

10. A compound or mixture according to claim 1 wherein the diphosphine is a diphosphine of formula IV, IVa, IVb, IVc or IVd $$R_7R_8P\text{—}R_9\text{—}PR_{10}R_{11} \quad (IV),$$

$$R_7R_8P\text{—}O\text{—}R_{12}\text{—}PR_{10}R_{11} \quad (IVa),$$

$$R_7R_8P\text{—}NR_c\text{—}R_{12}\text{—}PR_{10}R_{11} \quad (IVb),$$

$$R_7R_8P\text{—}O\text{—}R_{13}\text{—}O\text{—}PR_{10}R_{11} \quad (IVc),$$

$$R_7R_8P\text{—}NR_c\text{—}R_{13}\text{—}NR_c\text{—}PR_{10}R_{11} \quad (IVd),$$

wherein $R_7$, $R_8$, $R_{10}$ and $R_{11}$ are each independently of the others a hydrocarbon radical having from 1 to 20 carbon atoms that is unsubstituted or substituted by $C_1$–$C_6$alkyl, $C_1$–$C_6$alkoxy, halogen, $C_1$–$C_6$haloalkyl, $(C_1$–$C_{12}$alkyl$)_3$Si, $(C_6H_5)_3$Si, $C_1$–$C_6$haloalkoxy, —$NH_2$, phenyl$_2$N—, benzyl$_2$N—, morpholinyl, piperidinyl, pyrrolidinyl, $(C_1$–$C_{12}$alkyl$)_2$N—,-ammonium-$X_1^\ominus$, —$SO_3M_1$, —$CO_2M_1$, —$PO_3M_1$ or by —COO—$C_1$–$C_6$alkyl, wherein $M_1$ is an alkali metal or hydrogen and $X_1^\ominus$ is the anion of a monobasic acid;

$R_7$ and $R_8$ together and $R_{10}$ and $R_{11}$ together are a $C_1$–$C_4$alkylene radical that is unsubstituted or substituted by $C_1$–$C_6$alkyl, $C_1$–$C_6$alkoxy, $C_1$–$C_6$haloalkyl, $C_5$- or $C_6$-cycloalkyl, unsubstituted or $C_1$–$C_4$alkyl-, $C_1$–$C_4$alkoxy-, $C_1$–$C_4$haloalkyl- or halo-substituted phenyl, or by unsubstituted or $C_1$–$C_4$alkyl-, $C_1$–$C_4$alkoxy-, $C_1$–$C_4$haloalkyl- or halo-substituted benzyl;

$R_9$ is linear $C_2$–$C_4$alkylene that is unsubstituted or substituted by $C_1$–$C_6$alkyl, $C_5$- or $C_6$-cycloalkyl, phenyl, naphthyl or by benzyl; 1,2- or 1,3-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl; or 1,2- or 1,3-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl, and in the 1- and/or 2-positions or in the 3-position of which methylene or $C_2$–$C_4$alkylidene is bonded; 1,4-butylene substituted in the 2,3-positions by

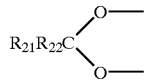

and unsubstituted or substituted in the 1,4-positions by $C_1$–$C_6$alkyl, phenyl or by benzyl, wherein $R_{21}$ and $R_{22}$ are each independently of the other hydrogen, $C_1$–$C_6$alkyl, phenyl or benzyl; 3,4- or 2,4-pyrrolidinylene or 2-methylene-pyrrolidin-4-yl the nitrogen atom of which is substituted by hydrogen, $C_1$–$C_{12}$alkyl, phenyl, benzyl, $C_1$–$C_{12}$alkoxycarbonyl, $C_1$–$C_8$acyl or by $C_1$–$C_{12}$alkylaminocarbonyl; or 1,2-phenylene, 2-benzylene, 1,2-xylylene, 1,8-naphthylene, 2,2'-dinaphthylene or 2,2'-diphenylene, each of which is unsubstituted or substituted by $C_1$–$C_4$alkyl; or $R_9$ is a radical of the formula

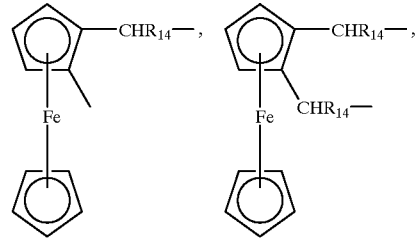

-continued

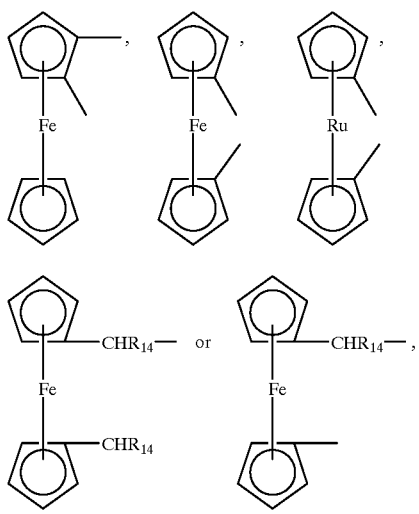

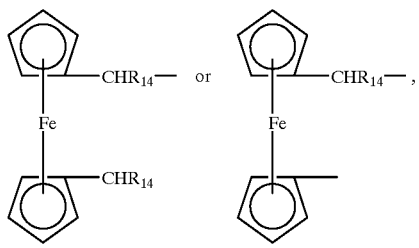

wherein $R_{14}$ is hydrogen, $C_1$–$C_8$alkyl, $C_1$–$C_4$fluoroalkyl, phenyl or phenyl having from 1 to 3 $C_1$–$C_4$alkyl or $C_1$–$C_4$alkoxy substituents;

$R_{12}$ is linear $C_2$- or $C_3$-alkylene that is unsubstituted or substituted by $C_1$–$C_6$alkyl, $C_5$- or $C_6$-cycloalkyl, phenyl, naphthyl or by benzyl; 1,2- or 1,3-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl; or 1,2- or 1,3-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl, and in the 1- and/or 2-positions or in the 3-position of which methylene or $C_2$–$C_4$alkylidene is bonded; 3,4- or 2,4-pyrrolidinylene or 3-methylene-pyrrolidin-4-yl the nitrogen atom of which is substituted by hydrogen, $C_1$–$C_{12}$alkyl, phenyl, benzyl, $C_1$–$C_{12}$alkoxycarbonyl, $C_1$–$C_8$acyl or by $C_1$–$C_{12}$alkylaminocarbonyl; or 1,2-phenylene, 2-benzylene or 1,2-, 2,3- or 1,8-naphthylene, each of which is unsubstituted or substituted by $C_1$–$C_4$alkyl; and $R_{13}$ is linear $C_2$alkylene that is unsubstituted or substituted by $C_1$–$C_6$alkyl, $C_5$- or $C_6$-cycloalkyl, phenyl, naphthyl or by benzyl; 1,2-cycloalkylene or -cycloalkenylene, -bicycloalkylene or -bicycloalkenylene having from 4 to 10 carbon atoms, each of which is unsubstituted or substituted by $C_1$–$C_6$alkyl, phenyl or by benzyl; 3,4-pyrrolidinylene the nitrogen atom of which is substituted by hydrogen, $C_1$–$C_{12}$alkyl, phenyl, benzyl, $C_1$–$C_{12}$-alkoxycarbonyl, $C_1$–$C_8$acyl or by $C_1$–$C_{12}$alkylaminocarbonyl; or 1,2-phenylene that is unsubstituted or substituted by $C_1$–$C_4$alkyl, or is a radical, less two hydroxy groups in the ortho positions, of a mono- or di-saccharide; and $R_c$ is hydrogen, $C_1$–$C_4$alkyl, phenyl or benzyl.

11. A compound or mixture according to claim 1 wherein the diphosphine DIP is a diphosphine of the formula

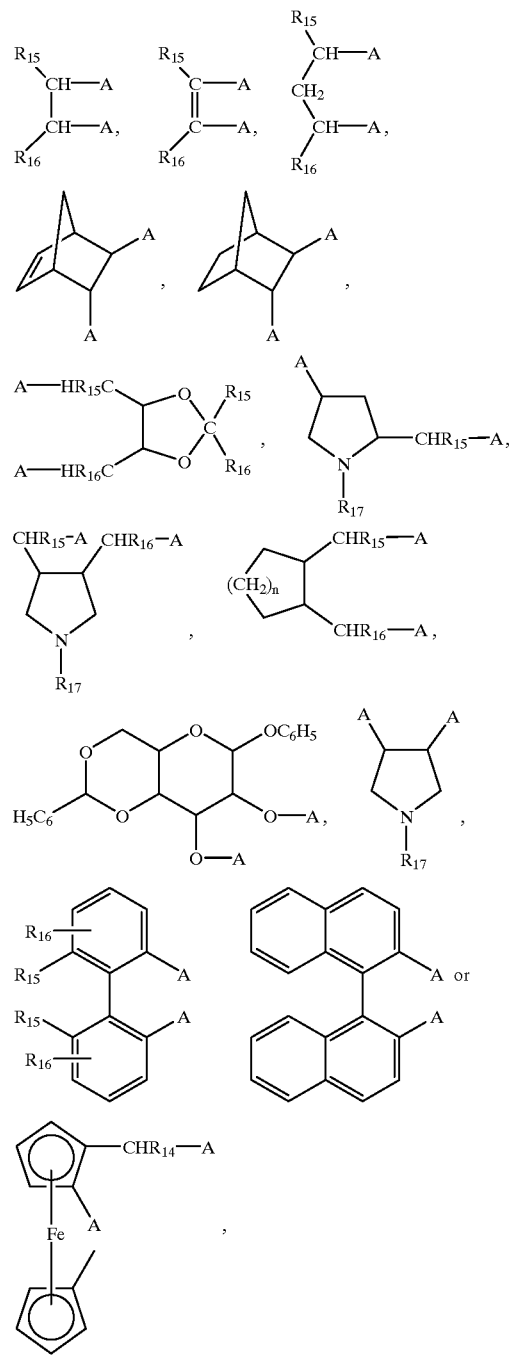

wherein $R_{15}$ and $R_{16}$ are each independently of the other hydrogen, $C_1$–$C_4$alkyl, phenyl, benzyl, or phenyl or benzyl each having from 1 to 3 $C_1$–$C_4$alkyl or $C_1$–$C_4$alkoxy substituents, $R_{14}$ is hydrogen, $C_1$–$C_4$alkyl, phenyl, benzyl, or phenyl or benzyl each having from 1 to 3 $C_1$–$C_4$alkyl or $C_1$–$C_4$alkoxy substituents, $R_{17}$ is hydrogen, $C_1$–$C_4$alkyl, phenyl, benzyl, $C_1$–$C_6$alkoxy-CO—, $C_1$–$C_6$alkyl-CO—, phenyl-CO—, naphthyl-CO— or $C_1$–$C_4$alkylNH-CO—, A may be identical or different groups —P(R)$_2$, wherein R is $C_1$–$C_6$alkyl, cyclohexyl, phenyl, benzyl, or phenyl or benzyl each having from 1 to 3 $C_1$–$C_4$alkyl, disubstituted amino, $C_1$–$C_4$alkoxy, —$CF_3$ or partially or fully fluorinated $C_1$–$C_4$alkoxy substituents, and N is 0, 1 or 2.

12. A compound or mixture according to claim 1 wherein the diphosphine is selected from ferrocenyl diphosphines wherein the secondary phosphine groups are either bonded directly or via a bridge group —$CR_aR_b$— in the ortho positions of a cyclopentadienyl ring or are each bonded to a cyclopentadienyl ring of a ferrocenyl.

13. A compound or mixture according to claim 12 wherein the diphosphine is a diphosphine of formula X (X)

wherein $R_{14}$ is hydrogen, $C_1$–$C_4$alkyl, phenyl, benzyl, or phenyl or benzyl each having from 1 to 3 $C_1$–$C_4$alkyl or $C_1$–$C_4$alkoxy substituents, and A may be identical or different groups —$P(R)_2$, wherein R is $C_1$–$C_6$alkyl, cyclohexyl, phenyl, benzyl, or phenyl or benzyl each having from 1 to 3 $C_1$–$C_4$alkyl, disubstituted amino, $C_1$–$C_4$alkoxy, —$CF_3$ or partially or fully fluorinated $C_1$–$C_4$alkoxy substituents.

14. A compound or mixture according to claim 13 wherein the diphosphine of formula X is chiral and $R_{14}$ is $C_1$–$C_4$alkyl, or phenyl or benzyl each having from 1 to 3 $C_1$–$C_4$alkyl or $C_1$–$C_4$alkoxy substituents, and A may be identical or different groups —$P(R)_2$, wherein R is $C_1$–$C_6$alkyl, cyclohexyl, phenyl, benzyl, or phenyl or benzyl each having from 1 to 3 $C_1$–$C_4$alkyl, disubstituted amino, $C_1$–$C_4$alkoxy, -$CF_3$ or partially or fully fluorinated $C_1$–$C_4$alkoxy substituents.

15. A compound or mixture according to claim 1 wherein the diphosphine is

{(R)-1-[(S)-2-(diphenylphosphino)ferrocenyl]}ethyl-di (3,5-dimethylphenyl)phosphine, {(R)-1-[(S)-2-(diphenylphosphino)ferrocenyl]}ethyl-di (3,5-dimethyl-4-N,N-dipropylaminophenyl)phosphine, {(R)-1-[(S)-2-(diphenylphosphino)ferrocenyl]}ethyl-di (3,5-diisopropyl-4-N,N-dimethylaminophenyl) phosphine, {(R)-1-[(S)-2-(diphenylphosphino)ferrocenyl]}ethyl-di (3,5-diisopropyl-4-N,N-dibenzylylaminophenyl) phosphine, {(R)-1-[(S)-2-(diphenylphosphino)ferrocenyl]}ethyl-di (3,5-dimethyl-4-N,N-dibenzylylaminophenyl) phosphine, {(R)-1-[(S)-2-(diphenylphosphino)ferrocenyl]}ethyl-di (3,5-dimethyl-4-(1'-pyrrolo)-phenyl)phosphine, {(R)-1-[(S)-2-(diphenylphosphino)ferrocenyl]}ethyl-di (3,5-dimethyl-4-N,N-dipentylaminophenyl)phosphine, {(R)-1-[(S)-2-(diphenylphosphino)ferrocenyl]}ethyl-di (3,5-dimethyl-4-N,N-dimethylaminophenyl) phosphine, {(R)-1-[(S)-2-di(4methoxyphenyl)phosphino)ferrocenyl]}ethyl-di(3,5-dimethyl-4-N,N-dimethylaminophenyl) phosphine, or 1,4-bis(diphenylphosphino)butane.

16. A compound or mixture according to claim 1 wherein in formula I X is Br or I.

17. A compound or mixture according to claim 1 wherein in formula I q and r are each 1.

18. A compound or mixture according to claim 1 wherein in formula Ia s is 0 and t is 1.

19. A compound or mixture according to claim 1 that is of formula Ib, Ic or Id (DIP)Ir(Z)$_3$ (Ib)

(DIP)IrH(Z) (Ic), (DIP)IrH(Z)$_2$ (Id), wherein Z is the anion of an organic oxy acid that contains a group C(=O)O, S(=O)O or P(=O)O in the anion.

20. A compound according to claim 1 wherein the organic oxy acid is of formula A or B $R_{100}$—$OSO_2$—OH (A), ($R_{100}$—O)$_2$P(O)—OH (B), wherein $R_{100}$ is the monovalent radical of an aliphatic, cycloaliphatic, cycloaliphatic-aliphatic, aromatic or araliphatic alcohol having from 1 to 20 carbon atoms.

21. A compound or mixture according to claim 1 wherein the organic oxy acid is of formula C, D or E $R_{101}$—S(O)$_k$—OH (C), $R_{101}$($R_{100}$O)$_l$P(O)—OH (D), $R_{102}$—C(O)—OH (E), wherein k is 1 or 2, l is 0 or 1, $R_{100}$ is the monovalent radical of an aliphatic, cycloaliphatic, cycloaliphatic-aliphatic, aromatic or araliphatic alcohol having from 1 to 20 carbon atoms, $R_{101}$ is an aliphatic, cycloaliphatic, cycloaliphatic-aliphatic, aromatic or araliphatic radical having from 1 to 20 carbon atoms that is unsubstituted or mono- or poly-substituted by $C_1$–$C_6$alkyl, $C_1$–$C_6$hydroxyalkyl, $C_1$–$C_6$haloalkyl, $C_1$–$C_6$alkoxy, $C_1$–$C_6$alkylthio, $C_5$- or $C_6$-cycloalkyl, $C_6$–$C_{10}$aryl, —OH, —F, Cl, Br, —CN, —$NO_2$ or by —C(O)O—$C_1$–$C_6$alkyl, it being possible for the substituents cycloalkyl and aryl to be substituted by $C_1$–$C_6$alkyl, $C_1$–$C_6$-alkoxy, —OH, —F, —Cl, —Br, —CN, —$NO_2$, $C_1$–$C_6$haloalkyl or by —C(O)O—$C_1$–$C_6$alkyl, and $R_{102}$ is hydrogen or has independently the same meaning as given for $R_{101}$.

22. A compound or mixture according to claim 21 wherein the organic acid is of formula C1 or E1

$R_{101}$—S(O)$_2$—OH (C1), $R_{101}$—C(O)—OH (E1), wherein $R_{101}$ is unsubstituted or $C_1$–$C_4$alkyl-, $C_1$–$C_4$alkoxy-, —OH—, —F—, —Cl—, —Br—, —$NO_2$—, —C(O)O—$C_1$–$C_4$alkyl-, cyclopentyl-, cyclohexyl- or phenyl-substituted $C_1$–$C_6$alkyl, wherein the substituents cyclopentyl, cyclohexyl or phenyl may be substituted by $C_1$–$C_4$alkyl, $C_1$–$C_4$alkoxy, —F, —Cl, —Br or by $C_1$–$C_4$haloalkyl.

23. A compound or mixture according to claim 22 wherein the organic acid is acetic acid, propionic acid, butyric acid, mono-, di- or tri-chloro- or mono-, di- or trifluoro-acetic acid, perfluoropropionic acid, cyclohexanecarboxylic acid, benzoic acid, mono-, di- or tri-methylbenzoic acid, fluoro- or chloro-benzoic acid, trifluoromethylbenzoic acid, phenylacetic acid, methanesulfonic acid, ethanesulfonic acid, propanesulfonic acid, butanesulfonic acid, mono-, di- or tri-chloro- or mono-, di- or tri-fluoromethanesulfonic acid, benzenesulfonic acid, mono-, di- or tri-methylbenzenesulfonic acid and fluoro- or chloro-benzenesulfonic acid.

24. A process for the preparation of a compound of formula I, Ia or Ib or of a mixture of at least two of those compounds according to claim 1, which comprises reacting an iridium compound of formula F

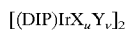   (F), wherein

DIP is as defined in claim 1,

X is Cl, Br or I,

Y is hydrogen, u is 2 or 3, v is 0 or 1, and the sum of u+v is 3, with at least equivalent amounts of a metal salt of formula G

   (G)

wherein Z is the anion of an organic oxy acid that contains a group C(═O)O, S(═O)O or P(═O)O in the anion, and Me is a metal ion that forms with the halide X a metal halide MeX that is not readily soluble.

25. A process according to claim 24 wherein Me in formula G is $A^{\oplus}$.

26. A process for the hydrogenation of an imine with hydrogen in the presence of iridium catalysts containing diphosphine ligands, with or without an inert solvent, wherein the hydrogenation is carried out in the presence of at least one compound of formula I, Ia or Ib, or of a mixture of at least two of those compounds

   (I),

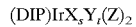   (Ia),

   (Ib), wherein

DIP is a ditertiary diphosphine, the two phosphine groups of which are bonded to a $C_2$-, $C_3$- or $C_4$-carbon chain, with the result that the diphosphine forms a 5- to 7-membered ring together with the Ir atom, X is Cl, Br or I, Y is a hydrogen atom, q and r are 0, 1 or 2 and the sum of q+r is 2, s and t are 0 or 1 and the sum of s+t is 1, and Z is the anion of an organic oxy acid that contains a group C(═O)O, S(═O)O or P(═O)O in the anion.

27. A process according to claim 26 wherein the imine is an imine of formula II

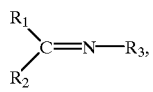   (II)

wherein $R_3$ is linear or branched $C_1$–$C_{12}$alkyl, cycloalkyl having from 3 to 8 ring carbon atoms; heterocycloalkyl bonded via a carbon atom and having from 3 to 8 ring atoms and 1 or 2 hetero atoms from the group O, S and $NR_6$; a $C_7$–$C_{16}$aralkyl bonded via an alkyl carbon atom or $C_1$–$C_{12}$alkyl substituted by the mentioned cycloalkyl or heterocycloalkyl or heteroaryl;

or wherein $R_3$ is $C_6$–$C_{12}$aryl, or $C_4$–$C_{11}$ heteroaryl bonded via a ring carbon atom and having 1 or 2 hetero atoms in the ring; $R_3$ being unsubstituted or substituted by —CN, —$NO_2$, F, Cl, $C_1$–$C_{12}$alkyl, $C_1$–$C_{12}$alkoxy, $C_1$–$C_{12}$alkylthio, $C_1$–$C_6$haloalkyl, —OH, $C_6$–$C_{12}$-aryl or -aryloxy or -arylthio, $C_7$–$C_{16}$-aralkyl or -aralkoxy or -aralkylthio, secondary amino having from 2 to 24 carbon atoms, —$CONR_4R_5$ or by —$COOR_4$, and the aryl radicals and the aryl groups in the aralkyl, aralkoxy and aralkylthio in turn being unsubstituted or substituted by —CN, —$NO_2$, F, Cl, $C_1$–$C_4$-alkyl, -alkoxy or -alkylthio, —OH, —$CONR_4R_5$ or by —$COOR_4$;

$R_4$ and $R_5$ are each independently of the other hydrogen, $C_1$–$C_{12}$alkyl, phenyl or benzyl, or $R_4$ and $R_5$ together are tetra- or penta-methylene or 3-oxapentylene;

$R_6$ has independently the same meaning as given for $R_4$;

$R_1$ and $R_2$ are each independently of the other a hydrogen atom, $C_1$–$C_{12}$alkyl or cycloalkyl having from 3 to 8 ring carbon atoms, each of which is unsubstituted or substituted by —OH, $C_1$–$C_{12}$alkoxy, phenoxy, benzyloxy, secondary amino having from 2 to 24 carbon atoms, —$CONR_4R_5$ or by —$COOR_4$; $C_6$–$C_{12}$aryl or $C_7$–$C_{16}$aralkyl that is unsubstituted or substituted as $R_3$, or —$CONR_4R_5$ or —$COOR_4$, wherein $R_4$ and $R_5$ are as defined hereinbefore; or $R_3$ is as defined hereinbefore and $R_1$ and $R_2$ together are alkylene having from 2 to 5 carbon atoms that is optionally interrupted by 1 or 2 —O—, —S— or —$NR_6$— radicals, and/or unsubstituted or substituted by ═O or as $R_1$ and $R_2$ above in the meaning of alkyl, and/or condensed with benzene, pyridine, pyrimidine, furan, thiophene or pyrrole; or $R_2$ is as defined hereinbefore and $R_1$ and $R_3$ together are alkylene having from 2 to 5 carbon atoms that is optionally interrupted by 1 or 2 —O—, —S— or —$NR_6$— radicals, and/or unsubstituted or substituted by ═O or as $R_1$ and $R_2$ above in the meaning of alkyl, and/or condensed with benzene, pyridine, pyrimidine, furan, thiophene or pyrrole.

28. A process according to claim 27 wherein the imine of formula II is a prochiral imine in which $R_1$ and $R_2$ are different.

29. A process according to claim 27 wherein in formula II $R_3$ is 2,6-di-$C_1$–$C_4$alkylphen-1-yl, $R_1$ is $C_1$–$C_4$alkyl, and $R_2$ is $C_1$–$C_4$alkyl, $C_1$–$C_4$alkoxymethyl or $C_1$–$C_4$alkoxyethyl.

30. A process according to claim 29 wherein the imine is an imine of formula Va, Vb or Vc

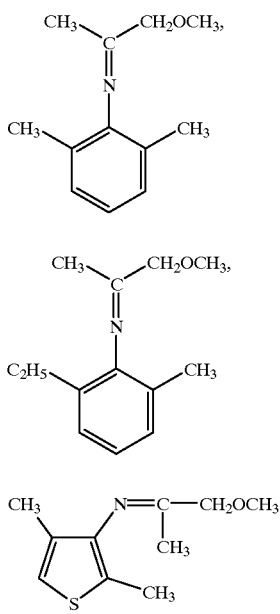

(Va)

(Vb)

(Vc)

31. A process according to claim 29 wherein the molar ratio of imine to iridium catalyst is from 5 000 000 to 10.

32. A process according to claim 29 wherein the molar ratio of imine to iridium catalyst is from 2 000 000 to 20.

33. A process according to claim 29 wherein the molar ratio of imine to iridium catalyst is from 1 000 000 to 100.

34. A process according to claim 26 wherein the reaction temperature is from −20 to 100° C.

35. A process according to claim 26 wherein the hydrogen pressure is from $2 \times 10^5$ to $1.5 \times 10^7$ Pa.

36. A process according to claim 26 which comprises the additional concomitant use of a soluble ammonium or metal chloride, bromide or iodide.

37. A process according to claim 26 wherein the hydrogenation takes place in the presence of an ammonium or metal halide in an amount from 0.01 to 200 equivalents, based on the iridium catalyst.

38. A process according to claim 26 that is carried out in the presence of a soluble ammonium or metal chloride, bromide or iodide and additionally an acid.

39. A process according to claim 38 wherein the molar ratio of imine to acid is from 1 000 000 to 100.

40. A process according to claim 38 wherein the acid is an inorganic acid, an organic acid, an inorganic or organic acidic ion exchanger or a solid acid that is other than an ion exchanger.

41. A process according to claim 39 wherein the inorganic acid is $H_2SO_4$, highly concentrated sulfuric acid (oleum), $H_3PO_4$, orthophosphoric acid, HF, HCl, HBr, HI, $HClO_4$, $HBF_4$, $HPF_6$, $HAsF_6$, $HSbCl_6$, $HSbF_6$ or $HB(phenyl)_4$.

42. A process according to claim 41 wherein the inorganic acid is $H_2SO_4$.

43. A process according to claim 39 wherein the organic acid is an aliphatic or aromatic, optionally halogenated carboxylic acid, sulfonic acid or phosphorus(V) acid having from 1 to 20 carbon atoms.

44. A process according to claim 43 wherein the organic acid is formic acid, acetic acid, propionic acid, butyric acid, benzoic acid, phenylacetic acid, cyclohexanecarboxylic acid, mono-, di- or tri-chioroacetic acid, mono-, di- or tri-fluoroacetic acid, chlorobenzoic acid, methanesulfonic acid, ethanesulfonic acid, benzenesulfonic acid, p-toluenesulfonic acid, chlorobenzenesulfonic acid, trifluoromethanesulfonic acid, methylphosphonic acid and phenylphosphonic acid.

45. A process according to claim 44 wherein the organic acid is $CF_3COOH$.

46. A process according to claim 26, wherein the hydrogenation takes place under elevated pressure.

47. A compound or mixture according to claim 1, wherein in formula Ia X is Br or I.

48. A compound or mixture according to claim 4, wherein the diphosphine is present as a pair of diastereoisomers.

* * * * *

UNITED STATES PATENT AND TRADEMARK OFFICE
CERTIFICATE OF CORRECTION

PATENT NO. : 6,008,393
DATED : December 28, 1999
INVENTOR(S) : RAFAEL SABLONG, et al.

It is certified that error appears in the above-identified patent and that said Letters Patent is hereby corrected as shown below:

Claim 11, col. 35, line 2, change "N" to -- n --.

Claim 20, col. 36, line 17, after "compound" insert -- or mixture --.

Claim 44, col. 40, line 26, replace "tri-chioroacetic" with -- tri-chloroacetic --.

Claim 44, col. 40, line 31, replace "and" with -- or --.

Signed and Sealed this

Twenty-first Day of November, 2000

Attest:

Q. TODD DICKINSON

Attesting Officer

Director of Patents and Trademarks